(12) United States Patent
Geisz et al.

(10) Patent No.: US 11,607,507 B2
(45) Date of Patent: Mar. 21, 2023

(54) METHOD AND SYSTEM FOR MEASURING PRESSURE IN A BODY CAVITY

(71) Applicant: Lexion Medical, LLC, St. Paul, MN (US)

(72) Inventors: Carl M. Geisz, Edina, MN (US); Rochelle M. Amann, Mendota Heights, MN (US)

(73) Assignee: LEXION MEDICAL, LLC, St. Paul, MN (US)

( * ) Notice: Subject to any disclaimer, the term of this patent is extended or adjusted under 35 U.S.C. 154(b) by 350 days.

(21) Appl. No.: 16/570,685

(22) Filed: Sep. 13, 2019

(65) Prior Publication Data

US 2020/0001025 A1   Jan. 2, 2020

Related U.S. Application Data

(63) Continuation-in-part of application No. 16/271,072, filed on Feb. 8, 2019, now Pat. No. 10,799,266, and
(Continued)

(51) Int. Cl.
*A61M 13/00* (2006.01)
*A61B 5/03* (2006.01)
(Continued)

(52) U.S. Cl.
CPC .............. *A61M 13/003* (2013.01); *A61B 5/03* (2013.01); *A61B 17/0218* (2013.01);
(Continued)

(58) Field of Classification Search
CPC ........ A61M 13/003; A61M 2205/3344; A61B 5/03; A61B 17/0218; A61B 17/3474
See application file for complete search history.

(56) References Cited

U.S. PATENT DOCUMENTS

| 5,328,458 A * | 7/1994 | Sekino ............... A61M 13/003 604/23 |
| 2005/0171470 A1* | 8/2005 | Kucklick .............. A61B 1/317 604/96.01 |

(Continued)

FOREIGN PATENT DOCUMENTS

EP        2 229 900 A1     9/2010

OTHER PUBLICATIONS

PCT Notification of Transmittal of the International Search Report and the Written Opinion of the International Searching Authority, or the Declaration with attached, International Search Report and Written Opinion of the International Searching Authority in International Application No. PCT/US2020/050038, dated Jan. 21, 2021, 17 pages.

*Primary Examiner* — Bradley J Osinski
(74) *Attorney, Agent, or Firm* — Baker Botts L.L.P.

(57) ABSTRACT

A method includes receiving, from a primary pressure sensor, a pressure measurement indicative of a pressure of a patient cavity and controlling, by an insufflator, a supply of the insufflation fluid to the patient cavity based on the pressure measurement from the primary pressure sensor. The method further includes delivering, by a trocar, the supplied insufflation fluid to the patient cavity via an access port, wherein: the access port comprises a seal and a retractor; and the access port facilitates access therethrough to the patient cavity.

20 Claims, 18 Drawing Sheets

Related U.S. Application Data a continuation-in-part of application No. 16/206,284, filed on Nov. 30, 2018, and a continuation-in-part of application No. 15/610,026, filed on May 31, 2017, now Pat. No. 10,646,667, said application No. 16/206,284 is a continuation-in-part of application No. 15/610,026, filed on May 31, 2017, and a continuation-in-part of application No. 15/251,511, filed on Aug. 30, 2016, now Pat. No. 10,595,897, said application No. 16/271,072 is a continuation-in-part of application No. 14/792,873, filed on Jul. 7, 2015, now Pat. No. 10,238,421.

(51) Int. Cl.
*A61B 17/02* (2006.01)
*A61B 17/34* (2006.01)

(52) U.S. Cl.
CPC ..... *A61B 17/3474* (2013.01); *A61M 2205/16* (2013.01); *A61M 2205/3344* (2013.01); *A61M 2205/50* (2013.01); *A61M 2205/52* (2013.01)

(56) References Cited

U.S. PATENT DOCUMENTS

| | | | |
|---|---|---|---|
| 2010/0280326 A1* | 11/2010 | Hess | A61B 17/3423 600/206 |
| 2015/0290403 A1* | 10/2015 | Torisawa | A61B 1/00131 604/26 |
| 2017/0056064 A1* | 3/2017 | Zergiebel | A61B 17/3474 |
| 2019/0091421 A1 | 3/2019 | Geisz et al. | |
| 2019/0175213 A1 | 6/2019 | Geisz et al. | |

* cited by examiner

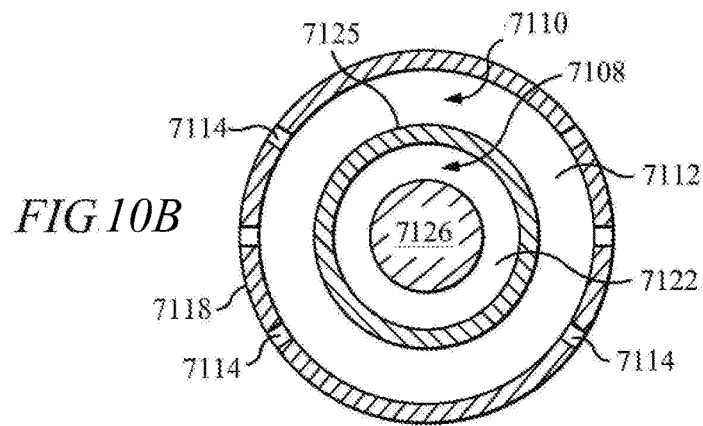
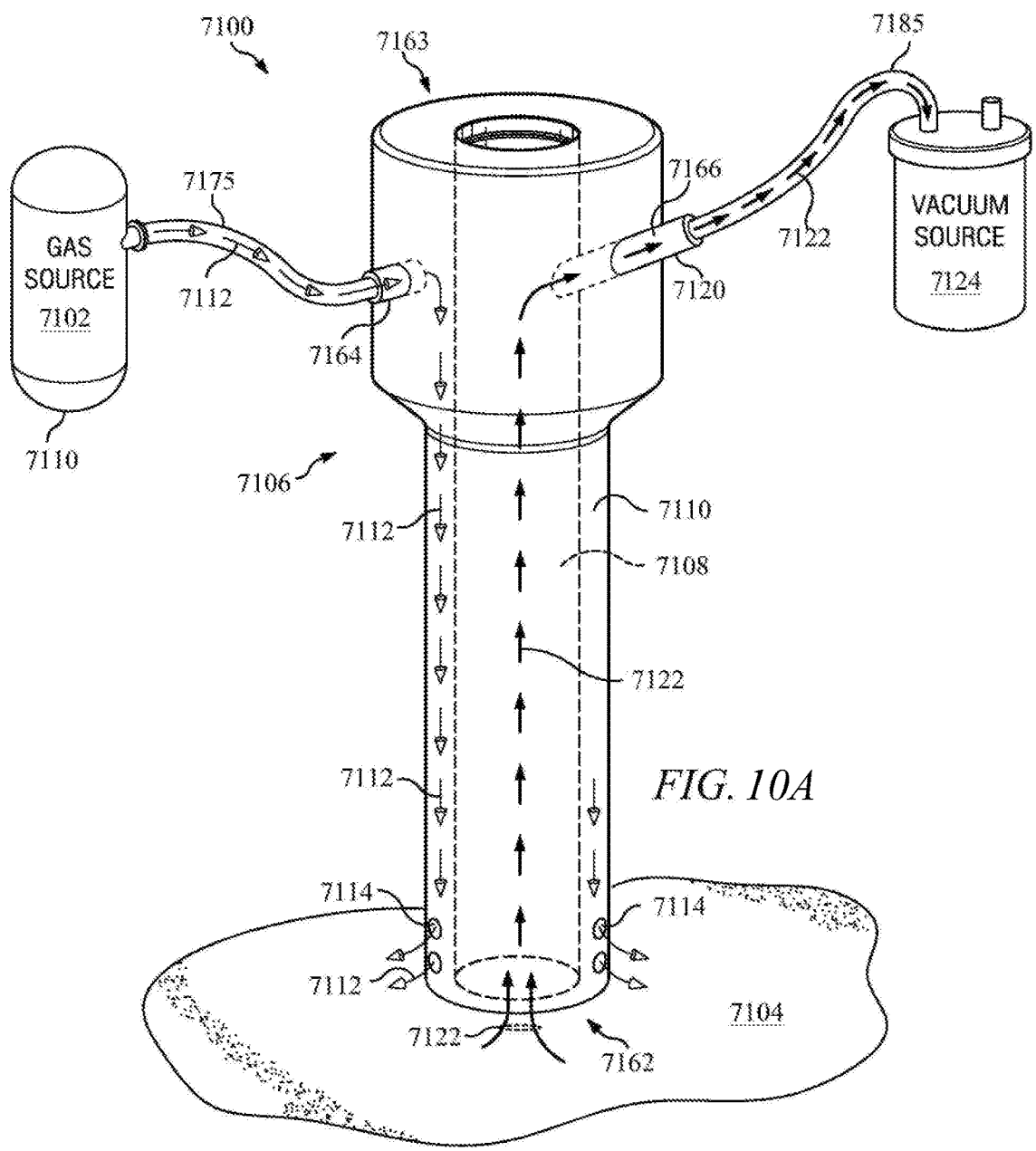

METHOD AND SYSTEM FOR MEASURING PRESSURE IN A BODY CAVITY

CROSS REFERENCE

This application is a continuation-in-part of U.S. application Ser. Nos. 16/206,284, 15/251,511, 15/610,026, and 16/271,072, which are incorporated by reference herein. Application Ser. No. 16/206,284, entitled "Method and System for Controlling Pressurization of a Patient Cavity Using a Pressure Sensor of a Medical Appliance," was filed on Nov. 30, 2018 and is a continuation-in-part application of U.S. application Ser. No. 15/610,026, entitled "Method and System for Controlling Pressurization of a Patient Cavity Using a Pressure Sensor in a Trocar," which was filed on May 31, 2017. U.S. application Ser. No. 15/251,511, filed Aug. 30, 2016, is entitled "Method and System For Measuring Pressure in a Body Cavity Using a Trocar." U.S. application Ser. No. 16/271,072, entitled "Method and System for Gas Maintenance to a Body Cavity Using a Trocar," was filed on Feb. 8, 2019 and is a continuation application of U.S. Ser. No. 14/792,873, filed on Jul. 7, 2015, is entitled "Method and System for Gas Maintenance to a Body Cavity Using a Trocar."

TECHNICAL FIELD

The present disclosure relates generally to medical procedures and more particularly to a method and system for measuring pressure in a body cavity.

BACKGROUND

Laparoscopic surgery is a standard procedure in hospitals. Abdominal and chest cavity operations are being performed with instruments inserted through small incisions into interior portions of the body. Such laparoscopic procedures are now considered the treatment of choice for operations such as the removal of the gall bladder, spleen, adrenal glands, uterus, and ovaries. These laparoscopic procedures are accomplished via access through a device typically known as a trocar.

A trocar facilitates the introduction of laparoscopic instruments into the abdomen or chest of the body. These instruments are typically introduced into regions under fluid pressure. Providing a fluid into a body cavity is referred to as insufflation, and the fluid (often a gas) is referred to herein as an insufflation fluid. The purpose of using such a device is to inflate or distend the body cavity to (1) allow the surgeon to explore the area in which the surgery will be performed and (2) provide a view of the site to be treated or observed. These trocars typically also allow for the insertion of an instrument via the innermost tube of the trocar. Examples of one or more trocars are provided in U.S. Pat. No. 8,715,219 (the '219 patent), U.S. Pat. No. 7,285,112 (the '112 patent), and U.S. Pat. No. 8,216,189 (the '189 patent), which are hereby incorporated by reference as if fully set forth herein.

Often, insufflation is performed by providing a regulated pressurized insufflation fluid to the peritoneal cavity (or other desirable patient cavity) via a cannula of the trocar. This insufflation fluid, typically carbon dioxide, is supplied to a connection on the trocar tube by a flexible hose attached thereto by an insufflator. Accurate control of the pressure inside the body cavity is important because it can prevent loss of visualization through the scope during the surgical procedure. Loss of visualization can slow down the surgery and is also potentially dangerous for the patient as the sharp surgical instruments can no longer be seen by the surgeon.

SUMMARY

According to one embodiment, a method of supplying insufflation fluid to a patient cavity includes receiving, from a primary pressure sensor, a pressure measurement indicative of a pressure of a patient cavity and controlling, by an insufflator, a supply of the insufflation fluid to the patient cavity based on the pressure measurement from the primary pressure sensor. The method further includes delivering, by a trocar, the supplied insufflation fluid to the patient cavity via an access port, wherein the access port comprises a seal and a retractor and the access port facilitates access therethrough to the patient cavity.

According to another embodiment, a system includes an insufflator, an access port, a primary pressure sensor, and a trocar. The insufflator includes a processor and a computer-readable media having logic stored thereon and is configured to supply insufflation fluid to a patient cavity. The access port includes a seal and a retractor and is configured to facilitate access therethrough to the patient cavity. The primary pressure sensor is configured to determine a pressure measurement indicative of a pressure of the patient cavity and the trocar is configured to receive the insufflation fluid supplied by the insufflator and deliver the insufflation fluid to the patient cavity via the access port. Furthermore, the insufflator is communicatively coupled to the primary pressure sensor and the logic stored on the computer-readable media is configured, when executed on the processor, to: receive the pressure measurement from the primary pressure sensor; and control the supply of the insufflation fluid to the patient based on the pressure measurement from the primary pressure sensor.

The teachings of the disclosure provide one or more technical advantages. Embodiments of the disclosure may have none, some, or all of these advantages. For example, the systems and methods described herein may permit real-time pressure sensing in applications where pressure sensing is extremely critical. One such application is a transanal minimally invasive surgery ("TAMIS") procedure. As another example, in some embodiments, a method and apparatus for measuring pressure in a patient cavity is provided that allows more accurate assessment of the pressure in a patient cavity due in part to the proximity of the pressure sensor to the patient cavity. Also, it is out of the gas flow stream which can create inaccurate pressure readings.

Other advantages will be apparent to those of skill in the art.

BRIEF DESCRIPTION OF THE DRAWINGS

For a more complete understanding of embodiments of the disclosure and the potential advantages thereof, reference is now made to the following written description taken in conjunction with the accompanying drawings, in which:

FIGS. 10A and 10B illustrate one embodiment of a system to supply an insufflation fluid to a patient cavity that uses a trocar having an inner lumen and an outer lumen in which the outer lumen allows for the insufflation fluid to be delivered to the patient cavity and the inner lumen provides a path for smoke to be removed from the patient cavity;

DETAILED DESCRIPTION OF THE DRAWINGS

The teachings of certain portions of the present disclosure recognize that controlling pressure in a body cavity may be effected more advantageously by measuring a pressure through a pressure sensor disposed within a trocar disposed within the body cavity and providing the measured pressure to a controller that can appropriately supply pressurized insufflation fluid to the body cavity. Measuring pressure using a pressure sensor disposed within the trocar provides a more accurate indication of the pressure in the body cavity and can alleviate pressure control problems that may be experienced through other techniques. Example embodiments are best understood by referring to FIGS. 1A through 1B of the drawings and the description below, like numerals being used for like and corresponding parts of the various drawings.

Figure 1A:
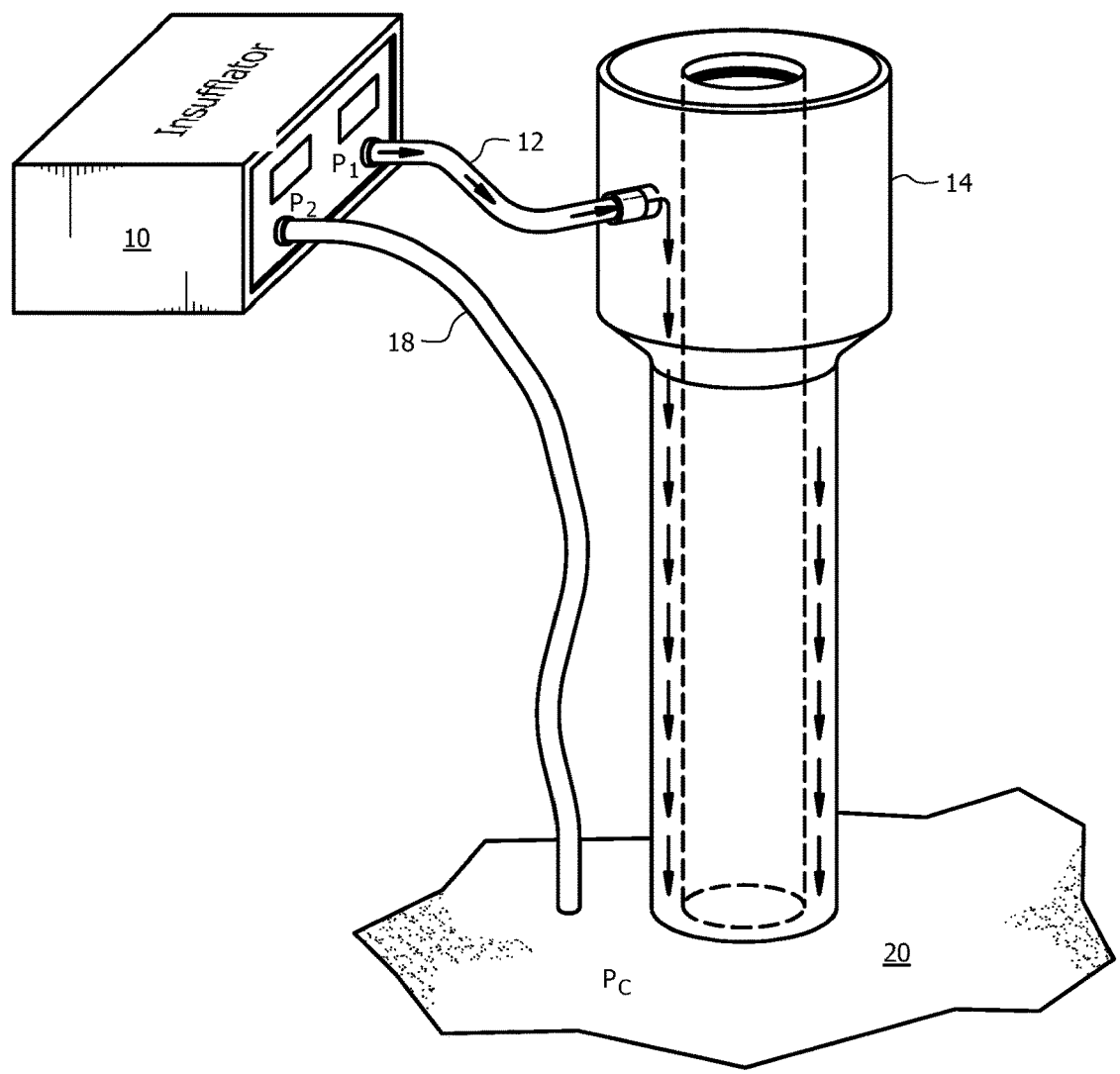
FIG. 1A is a schematic diagram illustrating the control of pressure in a body cavity according to a traditional approach.
Figure 1B:
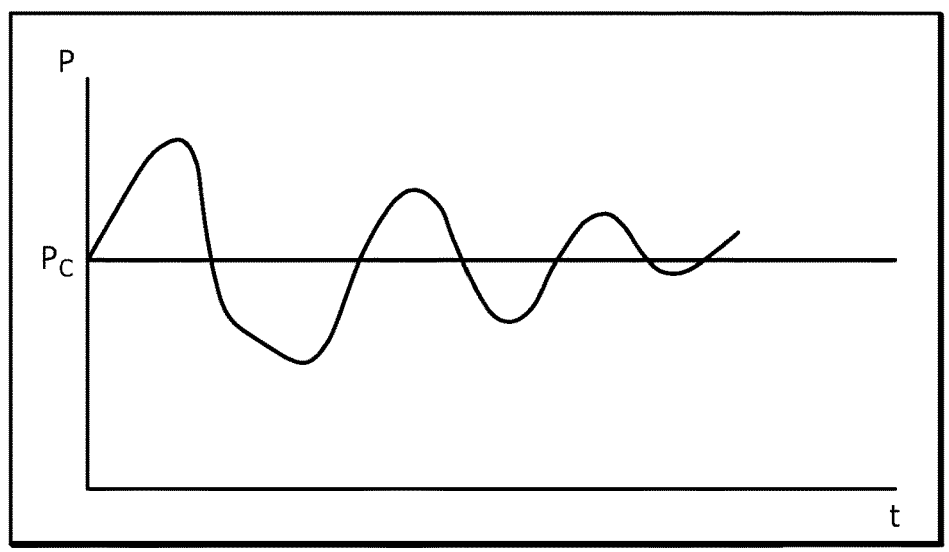
FIG. 1B is a graph illustrating pressure versus time for an example operation of the system of FIG. 1A.

FIG. 1A is a schematic diagram illustrating the control of pressure in a body cavity according to a traditional approach, and FIG. 1B is a graph illustrating pressure versus time for an example operation of the system of FIG. 1A. FIG. 1A shows an insufflator 10 connected to a patient, or body, cavity 20 through conduit 12 and a trocar 14. FIG. 1A also illustrates an alternative conduit 18, through which pressure can be measured.

It is desirable to control the pressure within body cavity 20, referred to as Pc, during an operation. One traditional approach for such pressure control is to provide an insufflation fluid to body cavity 20 by insufflator 10, through conduit 12 and trocar 14. In some implementations, insufflator 10 operates on an on/off basis, and the pressure Pc in body cavity 20 is desirably controlled based on the actual pressure Pc in body cavity 20. The traditional control approach, however, is to control supply of insufflation fluid from insufflator 10 to body cavity 20 based on a pressure P1, measured at insufflator 10. This pressure P1 is the pressure where conduit 12 meets insufflator 10, and thus serves as a proxy for pressure Pc in patient cavity 20. Due to pressure losses between insufflator 10 and patient cavity 20, the measured pressure P1 is not the same as the actual pressure Pc in patient cavity 20, particularly since pressurized insufflation fluid is provided by insufflator 10 through conduit 12. As an alternative traditional method, separate conduit 18 is used to measure P2, which is the pressure where conduit 18 meets insufflator 12. Unlike conduit 12, pressurized insufflation fluid is not provided through this conduit 18. Thus, P2 is a better indication of the pressure Pc in patient cavity 20 than P1 is. Nevertheless, both approaches are not as accurate as may be desired and can lead to undesirable results, such as those shown in FIG. 1B. Further, pressure control can become inaccurate or inoperable if conduit 18 becomes clogged or disconnected.

In FIG. 1B, pressure fluctuations over time are shown that can result from both of these traditional control procedures. These fluctuations occur due to differences between the actual Pc in body cavity 20 and P1 and P2. At high leak rates in the patient cavity they can prevent loss of visualization thru the scope during the surgical procedure. Loss of visualization can slow down the surgery, and is also potentially dangerous for the patient as the sharp surgical instruments can no longer be seen by the surgeon.

Figure 2A:
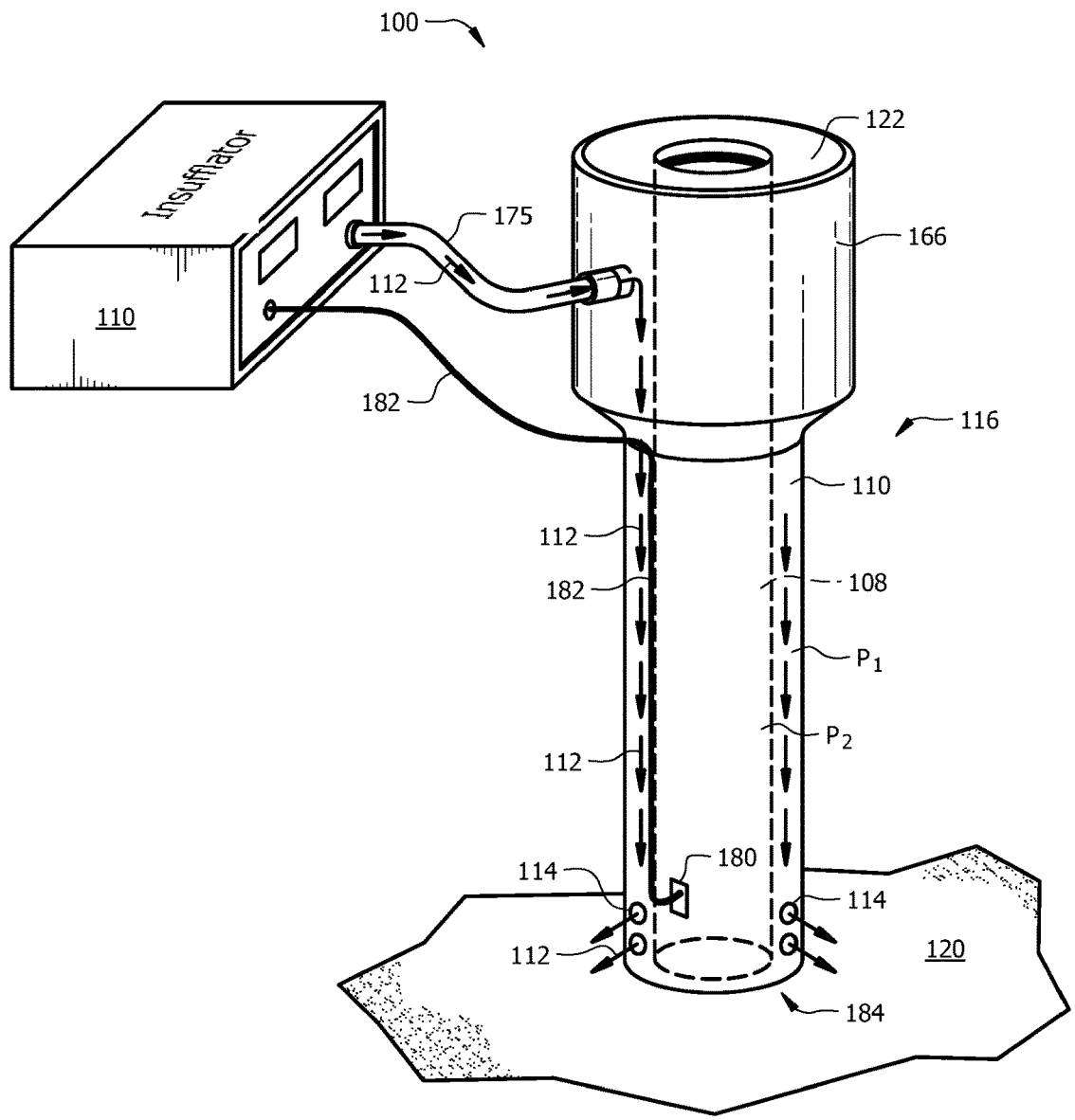
FIGS. 2A and 2B are schematic diagrams of a system for measuring pressure in a body cavity using a trocar.
Figure 2B:
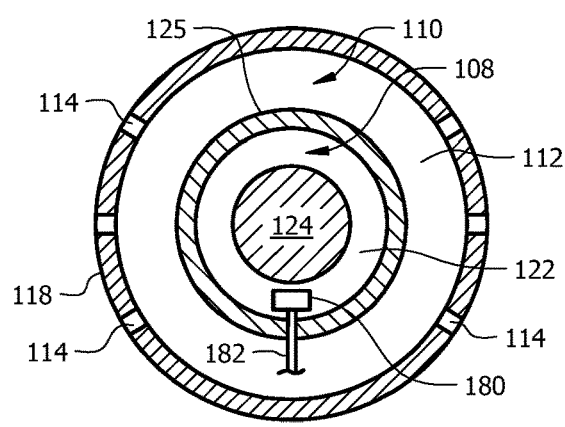

According to the teachings of the present disclosure, better pressure control of the pressure in a patient or body cavity can be achieved through use of a pressure sensor disposed in a trocar in the patient cavity, such as trocar 116 of FIGS. 2A and 2B. Disposing a pressure sensor in the trocar allows measurement of pressure at a location much closer to the patient cavity and therefore provides a better basis for determining the actual pressure in the patient cavity, and thus better pressure control.

FIGS. 2A and 2B illustrate one embodiment of a system 100 for controlling pressure Pc in a patient or body cavity 120. System 100 includes a trocar 116, an insufflator 110, a conduit 175 for supplying insufflation fluid to a portion of trocar 116, a pressure sensor 180 disposed within trocar 116, and a conductive connection 182, providing an electrical connection between pressure sensor 180 and insufflator 110. A distal end 184 of trocar 116 is inserted into patient cavity 120 while the proximal end 122 allows an instrument 124 to be inserted such that trocar 116 provides access to body cavity 120 for the instrument 124. Suitable seals may be positioned in or around trocar 116 for preventing or reducing leakage of fluid out of trocar 116. Patient cavity 120 may be accessed through an incision made with an obturator, which may be included in the same kit or package with trocars described herein.

Trocar 116 is formed with an inner tubular member, or inner lumen, 108 and an outer tubular member, or outer lumen, 110 in this embodiment. However, trocars without separate inner and outer lumens may also be used. Inner lumen 108 is separated from outer lumen 110 by an inner wall 125. Outer lumen 110 is surrounded by an outer wall 118. Outer wall 118 may be formed with one or more holes or apertures 114 near a distal end 162 of trocar 116. Insufflator 110 is a source of insufflation fluid and may include appropriate control functionality for adjusting the supply of insufflation fluid, such as in response to receiving signals indicative of the pressure in the body cavity. A surgical instrument 124 may be positioned within inner lumen 108 to allow access to patient cavity 120 by a surgeon using surgical instrument 124. Electrical connection 182, which may be an electrical wire or any other suitable form of electrical connection, can be disposed in any suitable location within trocar 116, including in inner lumen 108 or outer lumen 110. Placement of electrical connection 182 primarily within outer lumen 110 provides an additional advantage of protecting electrical connection 182 from possible damage by instrument 124.

According to the operation of one embodiment, insufflation fluid 102, which in one embodiment is carbon dioxide, is delivered by insufflator 110 to patient cavity 120 through conduit 175 and outer lumen 110, as indicated by arrows 112. Insufflation fluid 102 enters patient cavity 120 via apertures 114 in outer wall 118 of the trocar 116. Pressure is measured by pressure sensor 180 within inner lumen 108 of trocar 124, providing an approximation of the pressure Pc within body cavity 120. The measured pressure is communicated to insufflator 110 through electrical connection 182 through outer lumen 110, in this example. In one embodiment, pressure sensor 180 electrically couples to electrical connection 182 through apertures, although other forms of electrical coupling may be used, including wireless coupling. Based on the measured pressure, insufflator 110 may adjust the pressure Pc in body cavity 180 by, for example, providing or not providing additional insufflation fluid 102 to body cavity 120 or by adjusting the pressure or valve flow at which insufflation fluid 102 is provided by insufflator 110. Any desired form of control may be used by insufflator, including on/off control, P, P-D, and P-I-D control approaches. By measuring the pressure near the body cavity Pc through a pressure sensor disposed within trocar 116, better control of the pressure within body cavity 120 can be achieved, and undesirable cycling such as that shown in FIG. 1B can be reduced.

Figure 3:
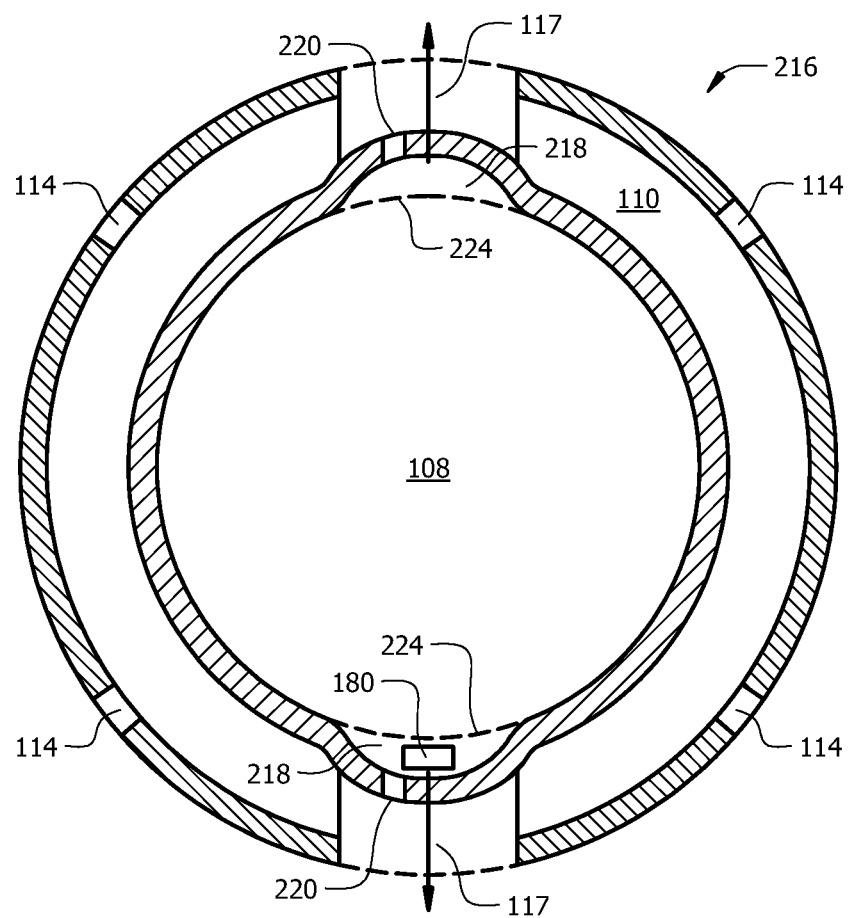
FIG. 3 is a cross sectional diagram of an alternative embodiment of the system of FIGS. 2A and 2B, showing an example cross section of a trocar.
Figure 4A:
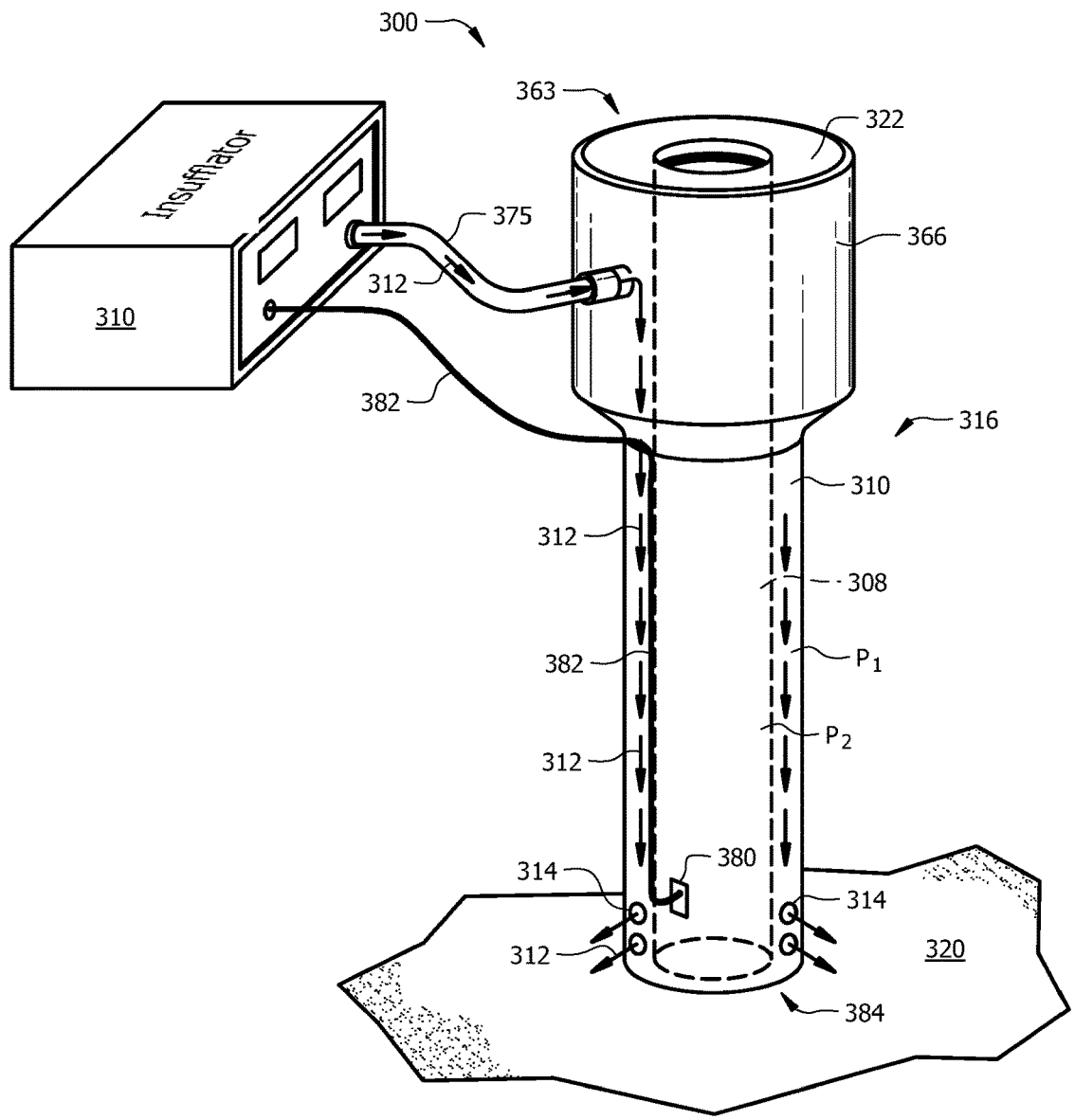
FIGS. 4A and 4B illustrate an alternative embodiment of a system for measuring pressure in a body cavity using a trocar with an outer tubular member having first and second channels (also referred to herein as "chambers")
Figure 4B:
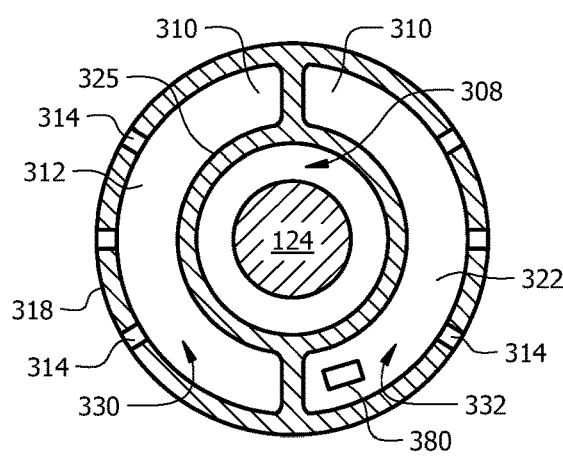
Figure 5:
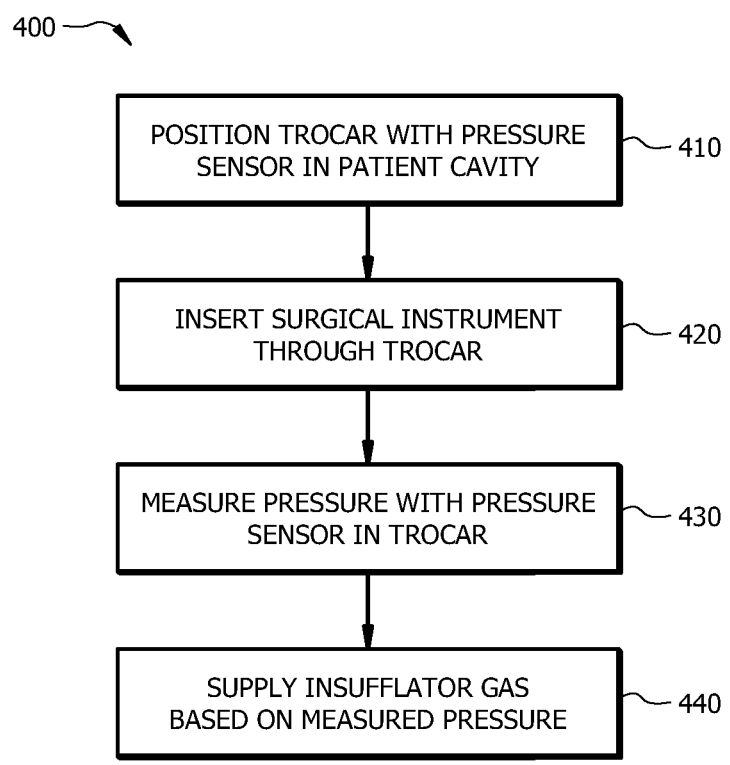
FIG. 5 is a flow chart illustrating a method for measuring pressure in a body cavity using a trocar.

Additional details and embodiments of systems and methods for providing pressure control of the pressure in a patient cavity are described below. FIG. 3 illustrates example details of portions of the system of FIGS. 2A and 2B, according to one embodiment. FIGS. 4A and 4B illustrate an alternative embodiment of a system for measuring pressure in a body cavity using a trocar with an outer tubular member having first and second channels, while FIG. 5 illustrates a method for controlling pressure in a body cavity.

FIG. 3 is a cross sectional diagram near the distal end 184 of one embodiment of a trocar 216 that may be used in the system of FIGS. 2A and 2B. Similar parts to those of trocar 116 have like reference numerals. As illustrated, trocar 216 includes at least one cutout region 218 into which pressure sensor 180 may be disposed. Placement of pressure sensor 180 in cutout region 218 protects pressure sensor 180 from damage that may occur when an instrument, such as instrument 124, is placed within inner lumen 108 of trocar. In this example embodiment cutout region 218 also protrudes into an area where the outer lumen 110 would otherwise be formed. The dotted line 224 forming part of cutout region 218 represents the missing portion of a generally circular inner lumen that would be formed without cutout region 218. Thus, this is one example of a configuration of cutout region 218 in which disposing pressure sensor 180 within cutout region 218 would make pressure sensor 180 generally inaccessible to an instrument 124 with a generally cross sectional area to protect pressure sensor 180 from damage. The cutout regions 218 also ensure that the obturator and/or instruments do not close off the inner lumen 108 from being in intimate contact with the body cavity 120.

In this embodiment, passages 220 between inner lumen 108 and outer lumen 110 are provided to allow gas flow in the event that inner lumen 108 becomes blocked, as indicated by arrows 117. The passages 220 and cutoffs 218 prevent closing off the pressure sensor from the body cavity 120.

FIGS. 4A and 4B illustrate another embodiment of a system 300 for controlling pressure Pc in a patient cavity 320 that uses a trocar having an inner lumen and an outer lumen with a plurality of chambers. System 300 is analogous to system 100, including a trocar 316, an insufflator 310, a conduit 312 for supplying insufflation fluid to a portion of trocar 316, a pressure sensor 380 disposed within trocar 316, and a conductive connection 382, providing an electrical connection between pressure sensor 380 and insufflator 310, with analogous portions of system 100 and system 300 having like reference numerals but trocar 316 is analogous to trocar 116, with analogous portions having analogous reference numerals, except that trocar 316 is formed with an inner lumen 308 and an outer lumen 310 having a plurality of chambers 330, 332. Outer wall 318 is formed with one or more holes or apertures 314 near a distal end 362 of trocar 306 that are associated with chamber 330. Outer wall 118 may also be formed with one or more holes or apertures 315 proximate distal end 362 of trocar 306 that are associated with chamber 332. Conductive connection 382 may be disposed primarily in chamber 330, 332 of out lumen 310, in inner lumen 308, or in other suitable locations.

Providing separate chambers 330 and 332 in outer lumen 310 allows placement of pressure sensor 380 in one of the outer chambers 330, 332 and allows supplying insufflation fluid in the other outer chamber 330, 332. This protects pressure sensor 380 from damage that could potentially be caused by instrument 124 due to insertion into inner lumen 108, while at the same time isolates pressure sensor 380 from supplied insufflation fluid 312, which might otherwise adversely affect the accuracy of the pressure measured by pressure sensor 380. In general, measuring pressure by pressure sensor 380 in a location within trocar 380 that does not also provide a conduit for insufflation fluid allows a more accurate estimation of Pc in patient cavity 320 because flow of gas creates a pressure drop along its path. This pressure drop required for gas to flow would create inaccurate pressure readings at the pressure sensor 380.

FIG. 5 is a flowchart illustrating a method of controlling pressure in a patient cavity. At step 410, a trocar is disposed into a patient cavity. In some embodiments, the trocar may be formed with an inner tubular member and an outer tubular member. In some of these embodiments, the outer tubular member may be formed with multiple separate chambers and in some embodiments the outer tubular member has only one distinct chamber. A pressure sensor is located within the trocar. In some embodiments the pressure sensor may be located in the inner tubular member or the outer tubular member. In some embodiments the pressure sensor is located near a distal end of the trocar, near the patient cavity, and also located in a location inaccessible to a surgical instrument that is inserted into the inner tubular member. At step 420, the surgical instrument is inserted into the trocar. At step 430, a pressure is measured by the pressure sensor disposed within the trocar, which is indicating of a pressure in the patient cavity. At step 440, based at least in part on the measured pressure, an insufflation fluid is supplied to the patient cavity by providing the insufflation fluid through the trocar. In one example, the pressure in the patient cavity can be increased by supplying more insufflation fluid or by supplying insufflation fluid at a higher pressure. Conversely, the pressure in patient cavity can be reduced by halting or reducing the flow of insufflation fluid or by reducing the pressure at which the insufflation fluid is supplied. The above steps may be performed in any desired order and may not necessarily be performed sequentially. For example, the pressure may be measured before, after, and/or during insertion of the surgical instrument. As another example, insufflation fluid may be supplied before, during, and/or after pressure measurement.

Thus, the systems of FIGS. 2A through 5 provide more accurate control of pressure in a patient cavity through use of a pressure sensor disposed within a trocar.

Additional details of systems 100 and 300 are described below for insufflation fluid 102, insufflation fluid source 170, trocars 116 and 316, open gas tubing connection 120, connection 164, conduit 175, conduit 185, and surgical instrument 124.

Insufflation fluid 102 may be any suitable gas used for insufflation purposes. In one example, insufflation case is carbon dioxide. Insufflation fluid source 170 may be any suitable source of insufflation fluid 102 at any suitable pressure.

Trocars 116, 216, and 316 may be any suitable as described herein. All trocars described herein may be open or closed at the distal end, as the application of the trocar would allow. Further, the trocars may or may not include apertures in their inner wall separating the outer lumen from the inner lumen. Further, all trocars described herein may be formed according to features described in the '219 patent, the '112 patent, and/or the '189 patent. Further, trocars 116 and 316 may be formed with a heater and/or humidifier therein.

Conduit 175 may be any suitable conduit for providing an insufflation fluid to a portion of a trocar. An example of conduit 175 includes flexible PVC tubing.

Conduit 185 may be any suitable conduit for providing a vacuum to a portion of a trocar. An example of conduit 185 is flexible PVC tubing.

Surgical instrument 124 may be any suitable instrument that may be used in surgery, including an obturator used to make an incision to obtain access to a body cavity.

Modifications, additions, or omissions may be made to systems 100, 300 without departing from the scope of the invention. The components of these systems may be integrated or separated. Moreover, the operations of these systems may be performed by more, fewer, or other components.

In addition to measuring a pressure indicative of a pressure of a patient cavity via a sensor positioned within a trocar, this disclosure recognizes certain benefits of measuring patient cavity pressure using multiple sensors positioned in, on, or through one or more medical appliances. As will be described in further detail with respect to FIGS. 6-9, insufflation fluid may be supplied to a patient cavity based on pressure measurements sensed by one or more of a primary pressure sensor and a backup pressure sensor as described in U.S. application Ser. Nos. 16/206,284 and 15/610,026.

Figure 6:
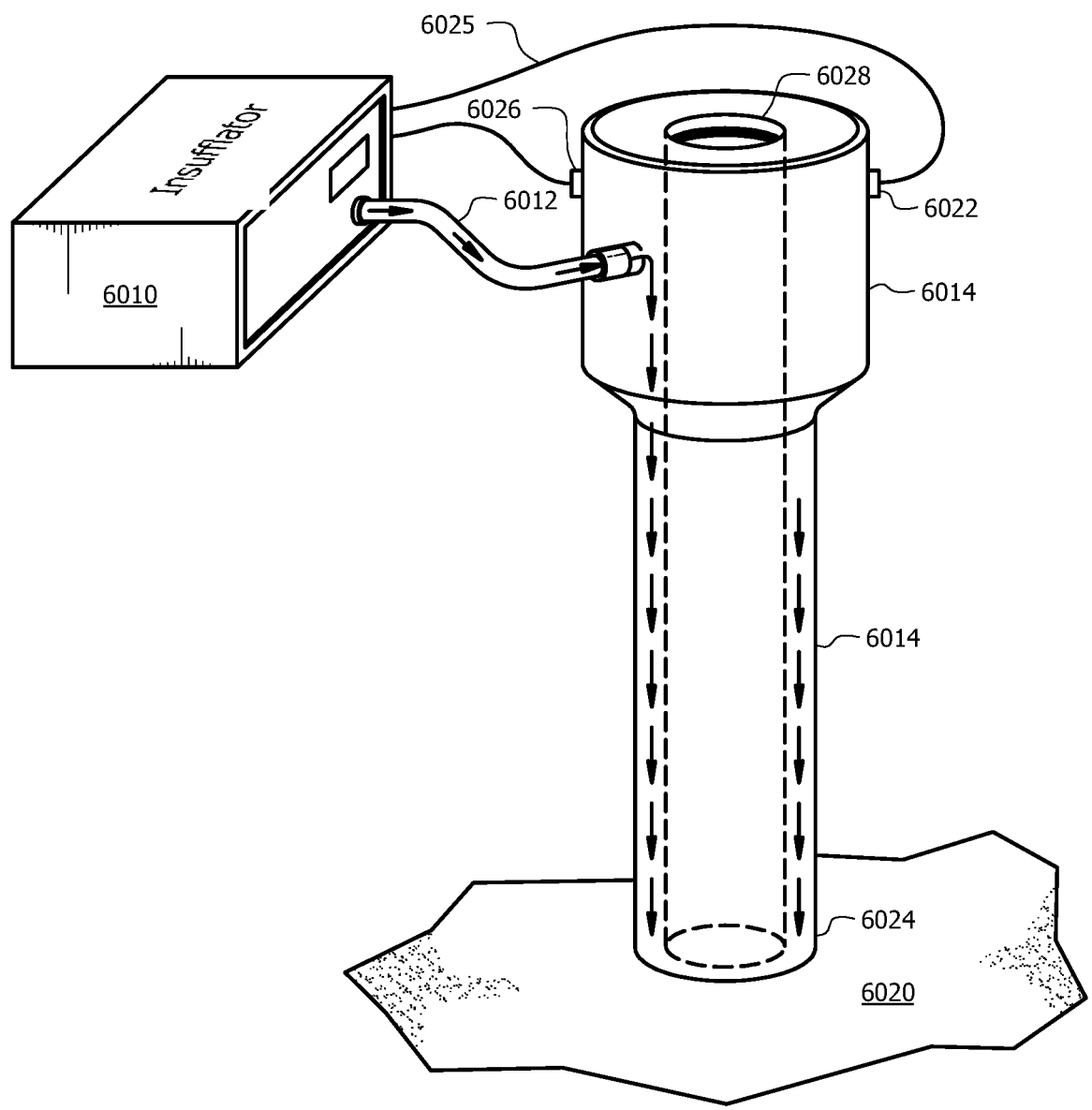
FIG. 6 is a schematic diagram showing a trocar having an associated pressure sensor, the distal end placed in the abdominal cavity of a patient.

FIG. 6 is a schematic diagram showing the distal end 6024 of a trocar 6014 placed in the abdominal cavity 6020 of a patient. In general, an insufflator 6010 supplies insufflation fluid through conduit 6012 and trocar 6014 to patient cavity 6020. Trocar 6014 allows insertion of a surgical instrument 6028 into patient cavity 6020.

Trocar 6014 has a primary pressure sensor 6022 on or associated with the trocar 6014. The location can be anywhere in, on, or through trocar 6014 or associated with trocar 6014; however, as described in greater detail below, in one embodiment primary pressure sensor 6022 is located on the exterior of trocar 6014 such that changes of pressure within trocar 6014 due to supply of insufflation fluid to patient cavity 6020 do not affect the pressure measured by primary pressure sensor 6022. In some embodiments, primary pressure sensor 6022 is an absolute pressure sensor that can measure pressure in patient cavity 6020 (if disposed within patient cavity 6020) or in the room in which the associated operation is taking place.

Primary pressure sensor 6022 is coupled to insufflator through any suitable technique, including a wired connection 6025 or a wireless connection. Primary pressure sensor 6022 supplies pressure data to insufflator 6010. Insufflator 6010 uses this pressure data to control the supply on insufflation fluid by insufflator 6010. In particular embodiments, this may include determining the change in height of trocar 6014 relative to changes in cavity pressure and thus the resulting change in height of patient cavity 6020, as described in greater detail in co-pending application Ser. No. 15/293,013 entitled Method and System for Controlling Pressurization of a Patient Cavity Using Cavity Distension Measured by a Pressure Sensor of a Trocar incorporated herein by reference. Additional details of certain portions of FIG. 6 are described below.

Insufflator 6010 may be any suitable source of insufflation fluid at any suitable pressure and may include a pressurized gas source. Insufflator may adjust the supply of insufflation fluid to patient cavity 6020 by adjusting the pressure and/or the volume of insufflation fluid supplied to patient cavity 6020. Insufflator may include appropriate hardware and/or software for processing signals indicative of pressures measured by primary pressure sensor 6022 and processing such signals to convert them into useful information, such as converting them into pressures, heights, and/or other data that can be used control the flow of insufflation fluid to patient cavity 6020, and further for processing such data to determine a desired pressure and/or volume of insufflation fluid supplied to patient cavity 6020 and for effecting such delivery.

Conduit 6012 may be any suitable conduit for providing an insufflation fluid to a portion of a trocar. An example of conduit 6012 includes flexible PVC tubing. The insufflation fluid may be any suitable gas used for insufflation purposes. In one example, insufflation case is carbon dioxide.

Trocar 6014 may be any suitable trocar through which insufflation fluid may be supplied to a patient cavity. Examples of one or more trocars are provided in U.S. Pat. No. 8,715,219 (the '219 patent), U.S. Pat. No. 7,285,112 (the '112 patent), and U.S. Pat. No. 8,216,189 (the '189 patent), which are hereby incorporated by reference as if fully set forth herein. Trocar 6014 may have a single lumen or may be formed with an inner tubular lumen and an outer tubular lumen such that insufflation fluid may be supplied through one of the lumens but not the other. Further, any of the lumens may be divided into multiple, separate chambers, such that gas in one chamber does not enter the other chamber. Examples of the above multiple lumens and multiple chambered trocars are described in U.S. application Ser. No. 14/792,873, entitled "Method and System for Gas Maintenance to a Body Cavity Using a Trocar," which is hereby incorporated by reference. Trocar 6014 may be open or closed at the distal end 6024, as the application of the trocar would allow.

Primary pressure sensor 6022 may be any sensor capable of sensing pressure or a change in pressure. Primary pressure sensor 6022 may measure absolute pressure or a pressure relative to some other pressure. In some embodiments, primary pressure sensor 6022 is an absolute sensor that can measure pressure in patient cavity 6020 (if disposed within patient cavity 6020) or in the room in which the associated operation is taking place. In particular embodiments, primary pressure sensor 6022 can measure absolute barometric pressures with an accuracy of less than 1 Pascal pressure and therefore have the ability to measure the relative changes in altitude of close to one inch. Such pressure sensors are readily available in the marketplace.

Figure 7A:
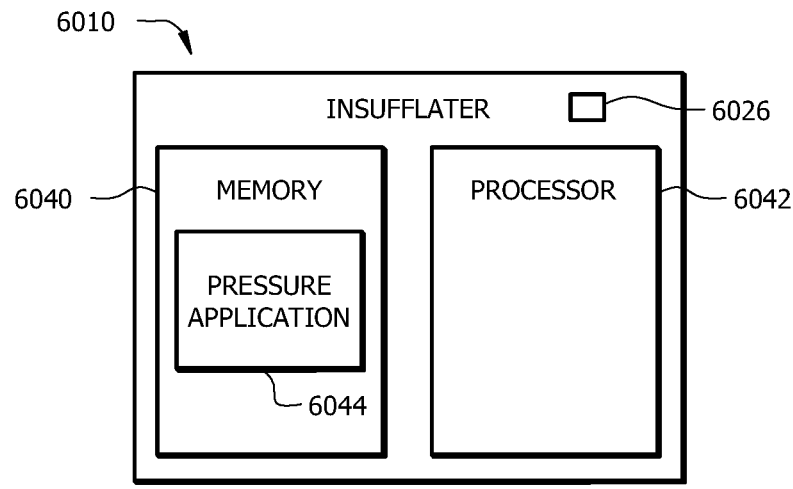
FIGS. 7A and 7B are block diagrams illustrating additional details of components of the system of FIG. 6 that may be used to effect pressure determination and resulting actions.
Figure 7B:
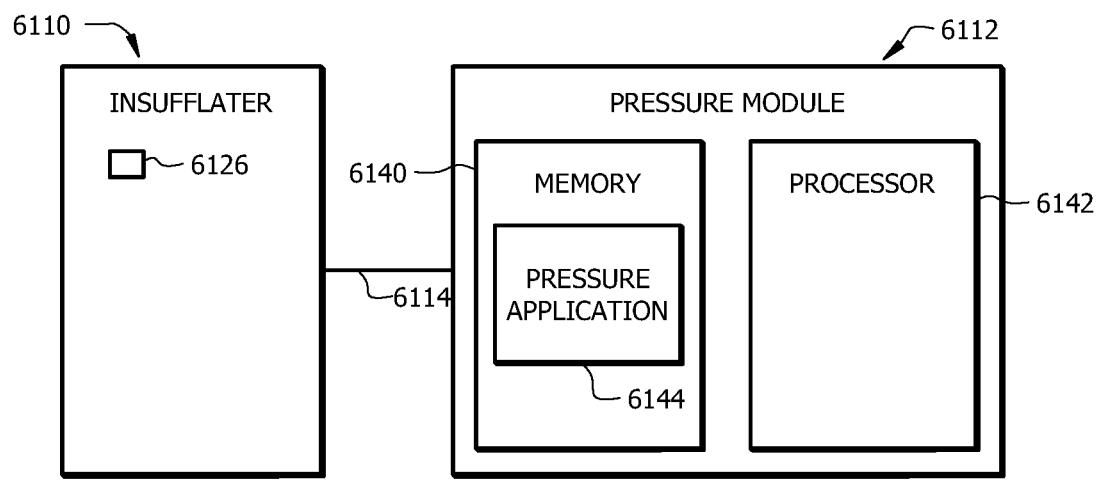

FIGS. 7A and 7B are block diagrams illustrating additional details of components of the system of FIG. 6 that may be used to effect pressure measurement and resulting insufflator control. FIG. 7A illustrates additional details of insufflator 6010, according to one embodiment. In this embodiment, insufflator 6010 includes a memory 6040 and a processor 6042 communicatively coupled to the memory 6040. Memory 6040 stores a pressure application 6044, which may include logic for effecting pressure and altitude determination as described with respect to the other FIGURES as well as control of the supply of insufflation fluid to patient cavity 6020. According to the teaching of the disclosure, a backup pressure sensor 6026 is provided. In one embodiment, insufflator 6010 includes a backup pressure sensor 6026. Backup pressure sensor 6026 may be used to measure pressure associated with trocar 6014 in the event or problems associated with primary pressure sensor 6022, as described in greater detail below in conjunction with FIG. 8. In another embodiment, backup pressure sensor 6026 is provided on trocar 6014, as illustrated in FIG. 6. The teachings of the disclosure recognize that primary pressure sensor 6022 may experience problems due to being located a larger distance from an associated processor, which leads to potential for erroneous readings and interference. In addition exposing primary pressure sensor 6022 to contamination, such as from blood and to humidity also contribute to potential problems being experienced by primary pressures sensor 6022. Backup pressure sensor 6026 may be any suitable pressure sensor, including the pressure sensors described above as being suitable as primary pressure sensor 6022.

FIG. 7B illustrates an alternative embodiment of the system of FIG. 6 in which an insufflator 6110 includes only standard features and is communicatively coupled through a connection 6114 to a pressure module 6112. Pressure module 6112 includes components analogous to those described with respect to FIG. 2A, including a backup pressure sensor 6126, but are included in this stand-alone pressure module. Connection 6114 between insufflator 6110 and pressure module 6112 may be wired or wireless. It will be understood that although a software-based system is illustrated in FIGS. 7A and 7B the logic described herein could instead be implemented through hardware circuits or a combination of hardware and software.

Figure 8:
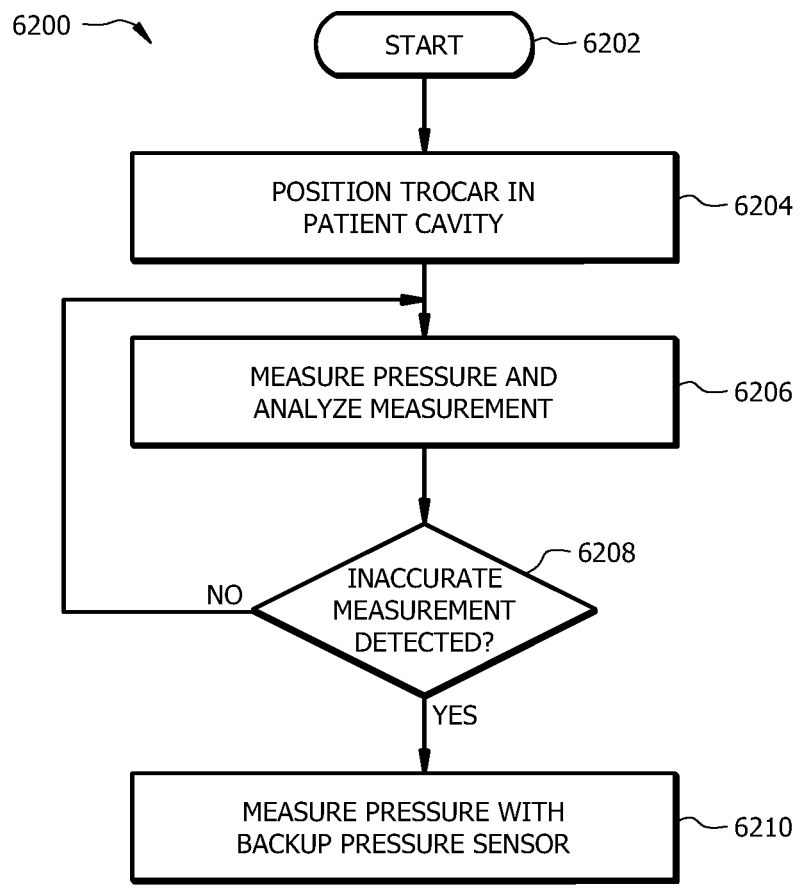
FIG. 8 is a flow chart illustrating a method that includes switching control of an insufflator to be based on pressure measurements of a backup pressure sensor.

FIG. 8 is a flow chart illustrating a method 6200 that includes use of a primary pressure sensor and a backup pressure sensor associated with a trocar. The method may utilize structural items such as those described in FIGURES through 7B or may use alternative structural items. Computational steps described below may be performed by any suitable computation device, including insufflator 6010 and pressure module 6112, for example.

The method begins at step 6202.

At step 6204, at least a portion of a trocar having a primary pressure sensor is positioned in a patient cavity. The pressure sensor in located on, or associated with, the trocar such that the primary pressure sensor can provide a direct measurement of a pressure in a patient cavity when a portion of the trocar is positioned in the patient cavity. At step 6206, the primary pressure sensor repeatedly measures a pressure within the patient cavity and communicates a signal indicative of the measurement to a processor associated with an insufflator. Also at step 6206, the processor analyzes the measured pressure for indications of whether the signals indicative of the measured pressure being inaccurate or otherwise suggesting that the primary pressure sensor is operating in a less than optimal manner. Any suitable factors may be considered in such analysis; however, certain factors that may indicate the primary pressure sensor is operating than a less than optimal manner include (1) whether the received signal is not within an expected range for the received signal; (2) whether error data is received, such as whether errors have occurred due to interference from a power signal, the wrong number of bits have been received, data is received in the wrong format, or data is received with improper spacing (3) whether proper acknowledgment bits are not received from the primary pressure sensor, (4) whether the received signal is not within an expected voltage range, (5) whether expected new updated status bits are not received, such as whether a signal has changed enough to indicate a new measurement has occurred as opposed to a signal being so close to a previous signal to indicate no new measurement has occurred; and (6) in the case of two or more pressure sensors located on or near trocar 6014, whether measurements by the two or more sensors are not within a certain range of each other.

At step 6208, a processor determines, whether the above analysis suggests the primary pressure sensor is not measuring accurately or otherwise not operating in a less than optimal fashion. If not, then processing returns to step 6206, and if so, the control by the insufflator is switched to be based on pressure sensed by a backup sensor at step 6210.

Although the pressure sensed by a backup pressure sensor 6210 is usually not as accurate a measure of the pressure within the patient cavity and as such not as desirable for use in controlling an insufflator associated with a trocar, when problems arise with a primary pressure sensor positioned on or associated with a trocar such the direct pressure measurements within a patient cavity can be made, it can be advantageous to at least temporarily switch control to be based on pressure measurements made by a backup pressure sensor located at the insufflator.

Upon completing step 6210, the method 6200 may conclude.

Thus, a method and system have been described that uses backup pressure sensor for pressure measurements associated with an insufflator when it is determined that pressure measurements associated with a primary pressure sensor may be inaccurate. By doing so, advantages associated with locating a pressure sensor nearer the patient cavity may be realized.

Although one embodiment has been illustrated and described in detail, it will be understood that various substitutions and alterations can be made therein without departing from the spirit and scope of the present invention, as defined by the following claims. For example, although primary pressure sensor 6022 has been described above as being located on trocar 6014, primary pressure sensor 6022 may be located on, in, or through other medical appliances as well. Such medical appliances may be or include one of: a needle (e.g., veress needle, fistula, Huber, spinal), a stapler, a grasper, a pair of scissors, a scalpel, a cutter, an electrode, an end seal, a probe, a multiple access port, and a single access port. Although this disclosure identifies certain types of medical appliances (including trocars 6014), this disclosure recognizes that primary pressure sensor 6022 may be located on, in, or through any suitable medical appliance. For example, this disclosure recognizes any medical appliance that can puncture the skin as a medical appliance.

Figure 9:
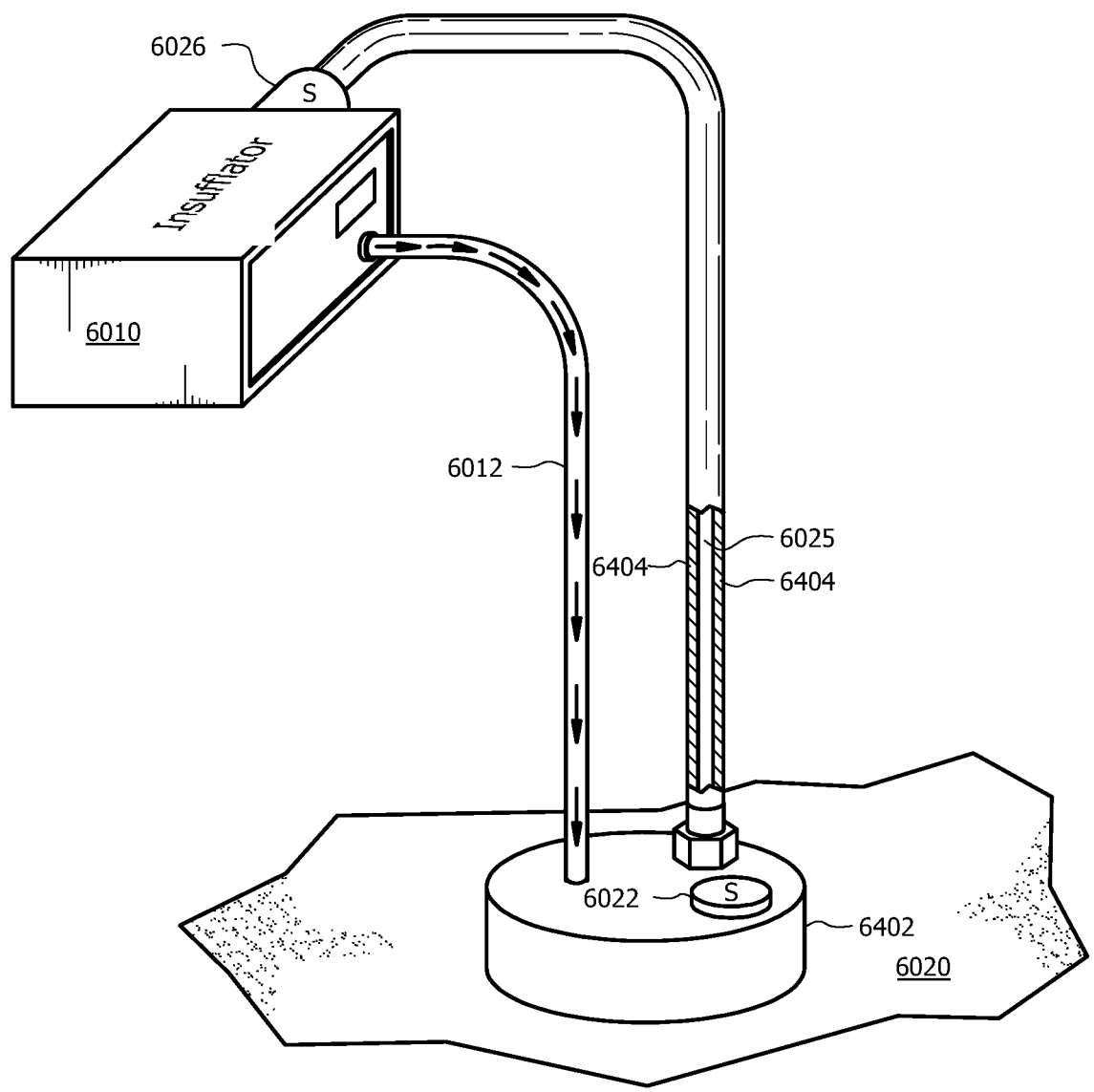
FIG. 9 is a schematic diagram showing a multiple access port having an associated pressure sensor, wherein the multiple access port provides access to the abdominal cavity of a patient.

FIG. 9 illustrates primary pressure sensor 6022 being part of or added to a medical port. A medical port 30 may be single access or multiple access. As suggested by their names, a single access port includes one access point by which to introduce fluids and/or medical instruments into a patient and a multiple access port includes more than one access point by which to introduce fluids and/or medical instruments into a patient. FIG. 9 illustrates a particular type of multiple access port known as a GelPort. As will be understood by a person of ordinary skill in the art, a GelPort Laparascopic System generally includes a GelSeal® cap and a wound protector/retractor. The wound protector/retractor is configured to extend through an incision site to patient cavity 6020 and the GelSeal® cap provides a seal for the wound protector/retractor. The GelSeal® cap is configured to be removably coupled to at least one end of the wound protector/retractor. As will also be understood by a person of ordinary skill in the art, GelSeal® cap may comprise a penetrable material that permits the insertion of one or more other medical appliances (e.g., trocar 6022, a scalpel, etc.).

In some embodiments, through appropriate tubing and/or sleeves, insufflation fluid may be introduced into patient cavity 6020 and smoke may be removed from patient cavity 6020 through GelSeal® cap.

As shown in FIG. 9, only GelSeal® cap 6402 of the GelPort is visible. This disclosure recognizes that primary pressure sensor 6022 may be included or added onto GelSeal® cap 6402 in a manner that permits pressure readings to be taken with respect to patient cavity 6020. As discussed above, primary pressure sensor 6022 or backup sensor 6026 may be coupled to a device (e.g., an insufflator 6010, a visual display) via wired connection 6025. In some embodiments, wired connection 6025 includes sheathing 6404 to shield wired connection 6025 from electromagnetic frequencies. All of a part of wired connection 6025 may be shielded. As illustrated in FIG. 9, wired connection 6025 is shielded by sheath 6404 and is coupled to backup sensor 6026 which provides a backup pressure measurement for primary pressure sensor 6022.

This disclosure also describes and illustrates measuring pressure in a patient cavity using one or more pressure sensors. In some embodiments, the one or more pressure sensors are employed in, on, or through medical appliances such as trocars. As will be understood by one of ordinary skill in the art, this disclosure anticipates employing pressure sensors in, on, or through any suitable trocar. In certain embodiments, one or more pressure sensors are employed in, on, or through trocars described and illustrated in U.S. application Ser. No. 14/792,873.

FIGS. 10A and 10B illustrate one embodiment of a system 7100 to supply an insufflation fluid 7102 to a patient cavity 7104 that uses a trocar having an inner lumen and an outer lumen in which the outer lumen allows for the insufflation fluid to be delivered to the patient cavity and the inner lumen provides a path for smoke to be removed from the patient cavity.

System 7100 includes a trocar 7106, an insufflation fluid source 7170, a vacuum source 7180, a conduit 7175 for supplying insufflation fluid 7102 to a portion of trocar 7106, and a conduit 7185 for applying a vacuum from vacuum source 7124 to a portion of trocar 7106. A distal end 7162 of trocar 7106 is inserted into patient cavity 7104 while the proximal end 7164 allows for an instrument 7126 to be inserted such that trocar 7106 provides access to body cavity 7104 for the instruments 7126. Suitable seals may be positioned in or around trocar 7106 for preventing or reducing leakage of fluid out of trocar 7106. Patient cavity 7104 may be accessed through an incision made with an obturator, which may be included in the same kit or package with trocars described herein.

Trocar 7106 is formed with an inner lumen 7108 and an outer lumen 7110. Inner lumen 7108 is separated from outer lumen 7110 by an inner wall 7125. Outer lumen 7110 is surrounded by an outer wall 7118. Outer wall 7118 may be formed with one or more holes or apertures 7114 near a distal end 7162 of trocar 7106. A surgical instrument 7126 may be positioned within inner lumen 7108 to allow access to patient cavity 7104 by a surgeon using surgical instrument 7126. An open gas tubing connection 7120 couples inner lumen 7108 to conduit 7185. Open gas tubing connection 7120 may include a vacuum break 7166. Tubing 7175 couples insufflation fluid source 7170 to outer lumen 7110 by connection 7164.

In operation, insufflation fluid 7102 is delivered to patient cavity 7104 from insufflation fluid source 7170 through conduit 7175 and outer lumen 7110, as indicated by arrows

7112. Insufflation fluid 7102 enters patient cavity 7104 via apertures 7114 in outer wall 7118 of the trocar 7106.

Smoke is sometimes present in patient cavity 104 due to electrocautery and other techniques (e.g. harmonic scalpels), and it is often desirable to remove such smoke from patient cavity 7104. The teachings of the disclosure recognize deficiencies associated with using a second trocar for smoke removal in addition to the trocar used to provide insufflation fluid to the patient.

Inner lumen 7108 of trocar 7106 allows for smoke in patient cavity 7104 to be removed using the same trocar 106 as is used for supplying insufflation fluid 7102 to patient cavity 7104. Smoke is removed through inner lumen 7108 via connection 7120, which couples inner lumen 7108 to conduit 7185, as indicated by arrows 7122. The smoke from patient cavity 7104 enters inner lumen 7108 through an opening at distal end 7162 of trocar 7106. The smoke can be vented into the operating room, filtered into the operating room, or vented out of the operating room via a vacuum source 7124. Inner lumen 7108 also allows for insertion of a surgical instrument 7126 at the same time as smoke is being removed.

Thus, trocar 7106 allows for supplying insufflation fluid 7102 to a patient cavity 7104 and removing smoke from the patient cavity 7104 without the use of multiple trocars 7106. Additional embodiments of systems and methods that allow supplying insufflation fluid 7102 to patient cavity 7104 along with cavity pressure measurement and/or smoke removal are described below in conjunction with FIGS. 2A through 7B. Additional details of certain portions of the described systems and methods are provided after the description of FIG. 16B.

Figure 11B:
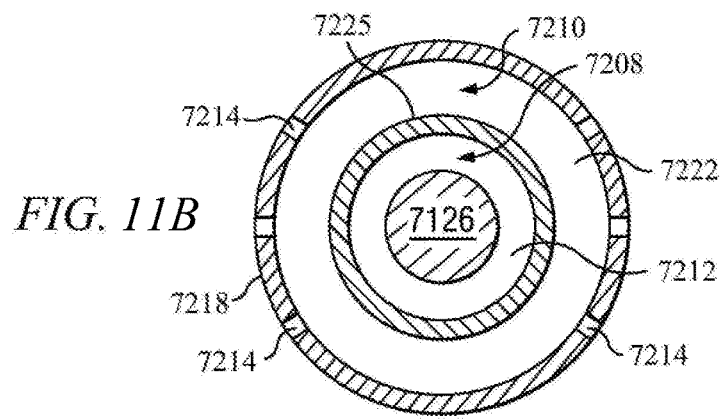
FIGS. 11A and 11B illustrate one embodiment of a system to supply an insufflation fluid to a patient cavity that uses a trocar having an inner lumen and an outer lumen in which the inner lumen allows for the insufflation fluid to be delivered to the patient cavity and the outer lumen provides a path for smoke to be removed from the patient cavity.
Figure 11A:
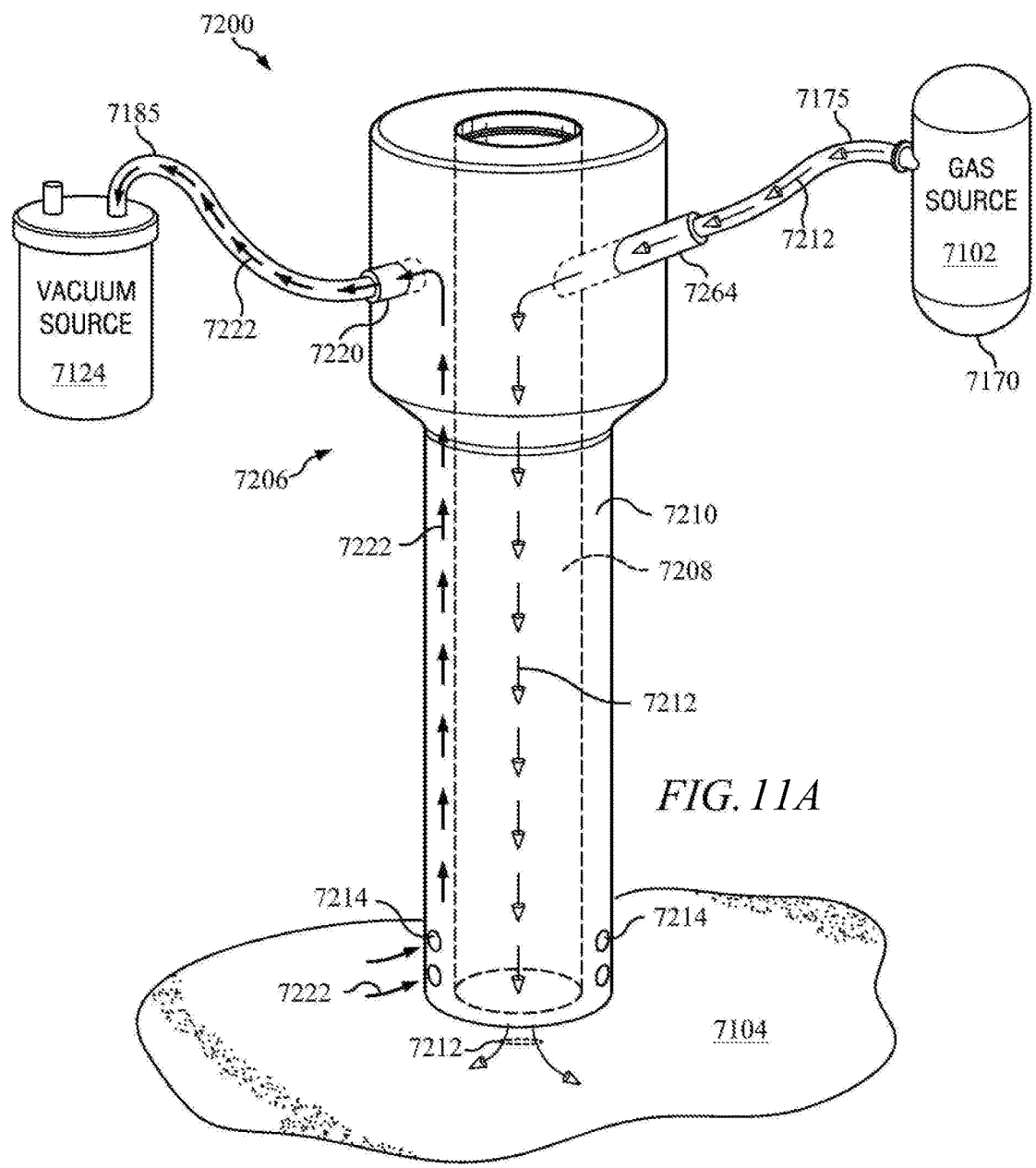

FIGS. 11A and 11B illustrate one embodiment of a system 7200 to supply an insufflation fluid 7102 to a patient cavity 7104 that uses a trocar having an inner lumen and an outer lumen in which the inner lumen allows for the insufflation fluid to be delivered to the patient cavity and the outer lumen provides a path for smoke to be removed from the patient cavity.

System 7200 includes a trocar 7206 having an inner lumen 7208 and an outer lumen 7210. Trocar 7206 is analogous to trocar 7106, with analogous portions having analogous reference numerals. System 7200 is analogous to system 7100, except that insufflation fluid 7102 is supplied to patient cavity 7104 via inner lumen 7208, rather than outer lumen 7110 as in system 7100, and smoke is removed from patient cavity 7104 via outer lumen 7210 rather than inner lumen 7108 as in system 7100. As such, system 7200 includes an open gas tubing connection 7220 between conduit 7185 and outer lumen. Connection 7220 is adapted to connect conduit 7185 to outer lumen 7210. And system 7200 includes a connection 7264 between conduit 7175 and inner lumen 7208 adapted to connect conduit 7175 to inner lumen 7208.

In operation, insufflation fluid 7102 is delivered to patient cavity 7104 from insufflation fluid source 7170 through conduit 7175 and inner lumen 7208, as indicated by arrows 7212. Insufflation fluid 7102 enters patient cavity 7104 via an opening at distal end 7262 of trocar 7206. Inner lumen 7208 also allows for the insertion surgical instrument 7126 at the same time as insufflation fluid 7102 is being delivered.

Outer lumen 7210 of trocar 7206 allows for smoke in patient cavity 7104 to be removed using the same trocar 7206 as is used for supplying insufflation fluid 7102 to patient cavity 7104. Smoke is removed through outer lumen inner 7210 via connection 7220, which couples outer lumen 7210 to conduit 7185, as indicated by arrows 7222. The smoke from patient cavity 7104 enters outer lumen 7210 through apertures 7214 in an outer wall 7218 of trocar 7206. The smoke can be vented into the operating room, filtered into the operating room, or vented out of the operating room via a vacuum source 7124.

Figure 12B:
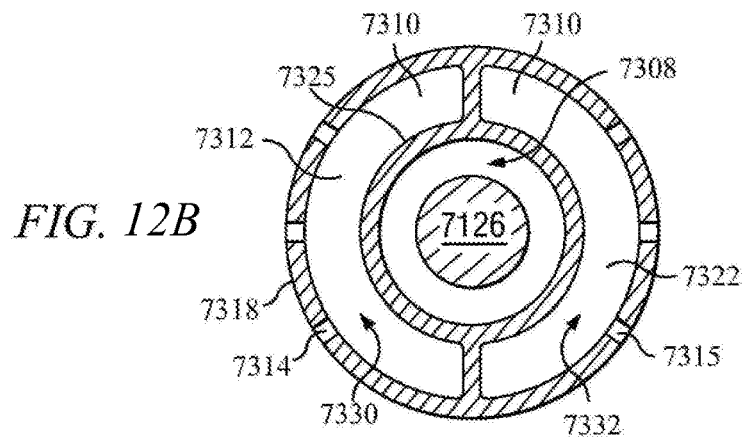
FIGS. 12A and 12B illustrate one embodiment of a system to supply an insufflation fluid to a patient cavity that uses a trocar having an inner lumen and an outer lumen with a plurality of chambers in which one of the chambers in the outer lumen allows for the insufflation fluid to be delivered to the patient cavity and the other chamber in the outer lumen provides a path for smoke to be removed from the patient cavity.
Figure 12A:
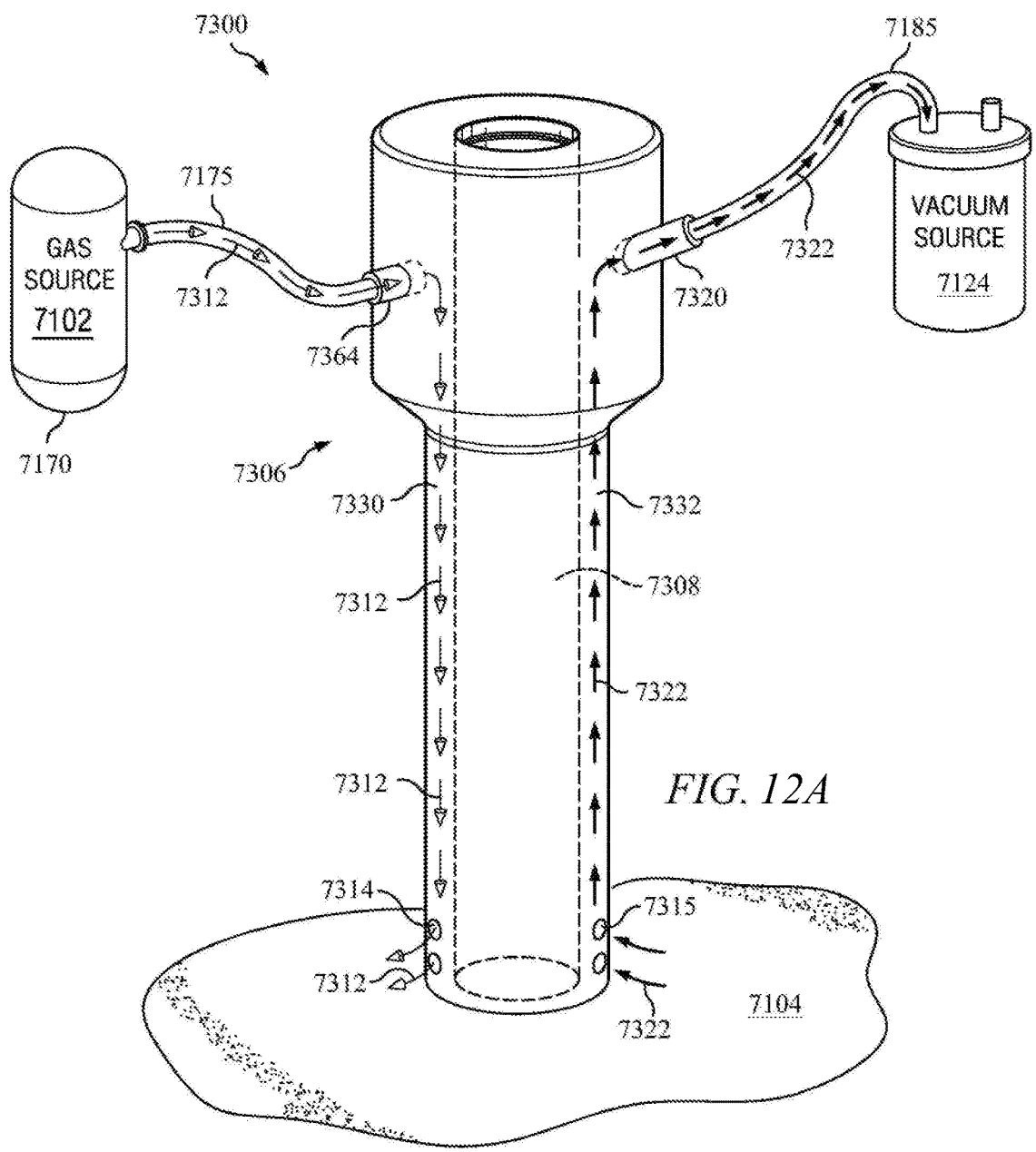

FIGS. 12A and 12B illustrate one embodiment of a system 7300 to supply an insufflation fluid 7102 to a patient cavity 7104 that uses a trocar having an inner lumen and an outer lumen with a plurality of chambers in which one of the chambers in the outer lumen allows for the insufflation fluid to be delivered to the patient cavity and the other chamber in the outer lumen provides a path for smoke to be removed from the patient cavity.

System 7300 includes a trocar 7306. Trocar 7306 is analogous to trocar 7106, with analogous portions having analogous reference numerals, except that trocar 7306 is formed with an inner lumen 7308 and an outer lumen 7310 having a plurality of chambers 7330, 7332. Outer wall 7318 is formed with one or more holes or apertures 7314 near a distal end 7362 of trocar 7306 that are associated with chamber 7330. Outer wall 7118 may also be formed with one or more holes or apertures 7315 proximate distal end 7362 of trocar 7306 that are associated with chamber 7332. System 7300 is analogous to system 7100, with analogous portions having analogous reference numerals, except that system 7300 includes an open gas tubing connection 7320 adapted to connect to chamber 7332 of outer lumen 7310 to conduit 7185. And, system 7300 includes a connection 7364 adapted to connect conduit 7312 to chamber 7330 of outer lumen 7310.

In operation, insufflation fluid 7102 is delivered to patient cavity 7104 from insufflation fluid source 7170 through conduit 7175 and chamber 7330 of outer lumen 7310, as indicated by arrows 7312. Insufflation fluid 7102 enters patient cavity 7104 via apertures 7314 in an outer wall 7318 of the trocar 7106.

The other chamber in outer lumen 7310, chamber 7332, allows for smoke in patient cavity 7104 to be removed using the same trocar 7306 as is used for supplying insufflation fluid 7102 to patient cavity 7104. Smoke is removed through chamber 7332 of outer lumen 7310 via connection 7320, which couples chamber 7332 of outer lumen 7308 to conduit 7185, as indicated by arrows 7322. The smoke from patient cavity 104 enters chamber 7332 of outer lumen 7108 through apertures 7315 in outer wall 7318 of trocar 7306. The smoke can be vented into the operating room, filtered into the operating room, or vented out of the operating room via a vacuum source 7124.

Inner lumen 7308 allows for insertion of surgical instrument 7126 at the same time as smoke is being removed and/or at the same time insufflation fluid is being supplied to patient cavity 7104.

Figure 13B:
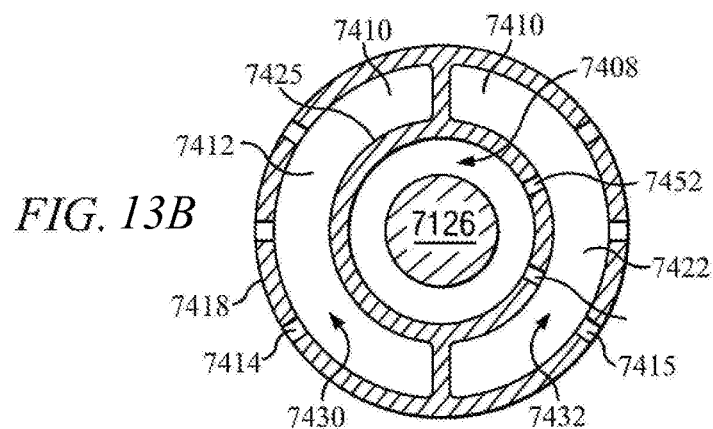
FIGS. 13A and 13B illustrate one embodiment of a system to supply an insufflation fluid to a patient cavity that uses a trocar having an inner lumen and an outer lumen with a plurality of chambers in which one of the chambers in the outer lumen allows for the insufflation fluid to be delivered to the patient cavity and the other chamber in the outer lumen allows pressure measurement of the patient cavity.
Figure 13A:
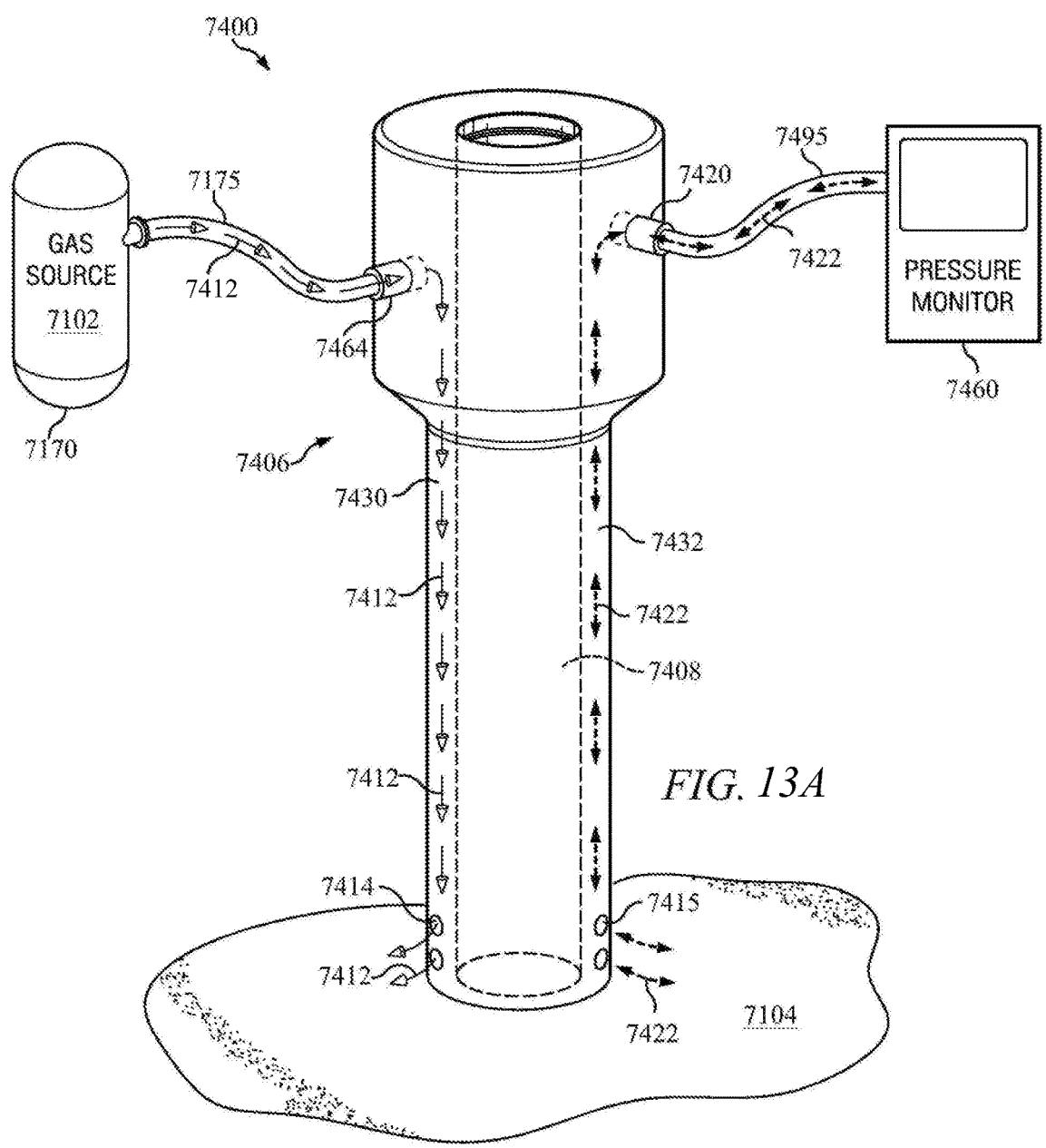

FIGS. 13A and 13B illustrate one embodiment of a system 7400 to supply an insufflation fluid 7102 to a patient cavity 7104 that uses a trocar having an inner lumen and an outer lumen with a plurality of chambers in which one of the chambers in the outer lumen allows for the insufflation fluid to be delivered to the patient cavity and the outer chamber in the outer lumen allows pressure measurement of the patient cavity.

System 7400 of FIGS. 13A and 13b is analogous to system 7300 of FIGS. 12A and 12B, except that chamber 7432 of outer lumen 7410 is used to effect pressure measurement of patient cavity 7104, as opposed to chamber 7332 being used to remove smoke from patient cavity 7104. As such system 7400 includes a monitor 7460 for measuring pressure that is connected to trocar 7406 by a suitable conduit 7495 for such a pressure measurement. Connection 7420 couples conduit 7495 to inner lumen chamber 7432. Trocar 7406 is analogous to trocar 7306, with analogous portions having analogous reference numerals. Connection 7464 may be adapted to couple outer chamber 7432 to conduit 7185.

In operation, insufflation fluid 7102 is delivered to patient cavity 7104 from insufflation fluid source 7170 through conduit 7175 and chamber 7430 of outer lumen 7410, as indicated by arrows 7412. Insufflation fluid 7102 enters patient cavity 7104 via apertures 7414 in an outer wall 7418 of the trocar 7406.

The other outer lumen chamber, chamber 7432, allows for pressure measurement by creating a direct connection from patient cavity 7104 through apertures 7415 to a monitor 7460 external to the patient, as illustrated by bi-directional arrows 7450. The direct connection has a minimal pressure drop to ensure accurate measurement. Outer lumen 7410 may or may not be connected to inner lumen 7408 via one or more holes 7452 in inner wall 7425.

Figure 14B:
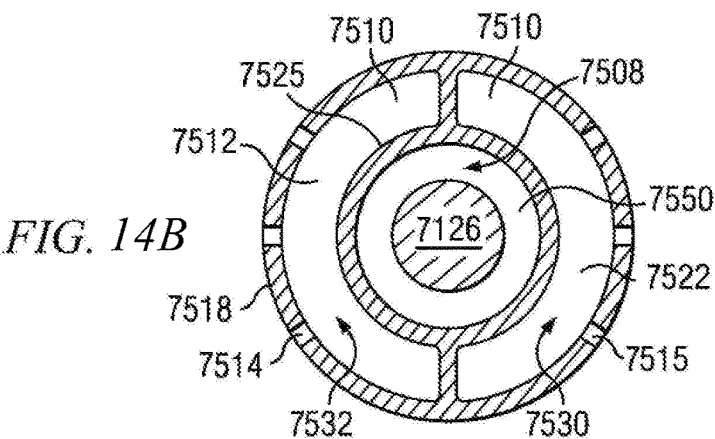
FIGS. 14A and 14B illustrate one embodiment of a system to supply an insufflation fluid to a patient cavity that uses a trocar having an inner lumen and an outer lumen with a plurality of chambers in which one of the chambers in the outer lumen allows for the insufflation fluid to be delivered to the patient cavity, the other chamber in the outer lumen provides a path for smoke to be removed from the patient cavity, and the inner lumen allows pressure measurement of the patient cavity.
Figure 14A:
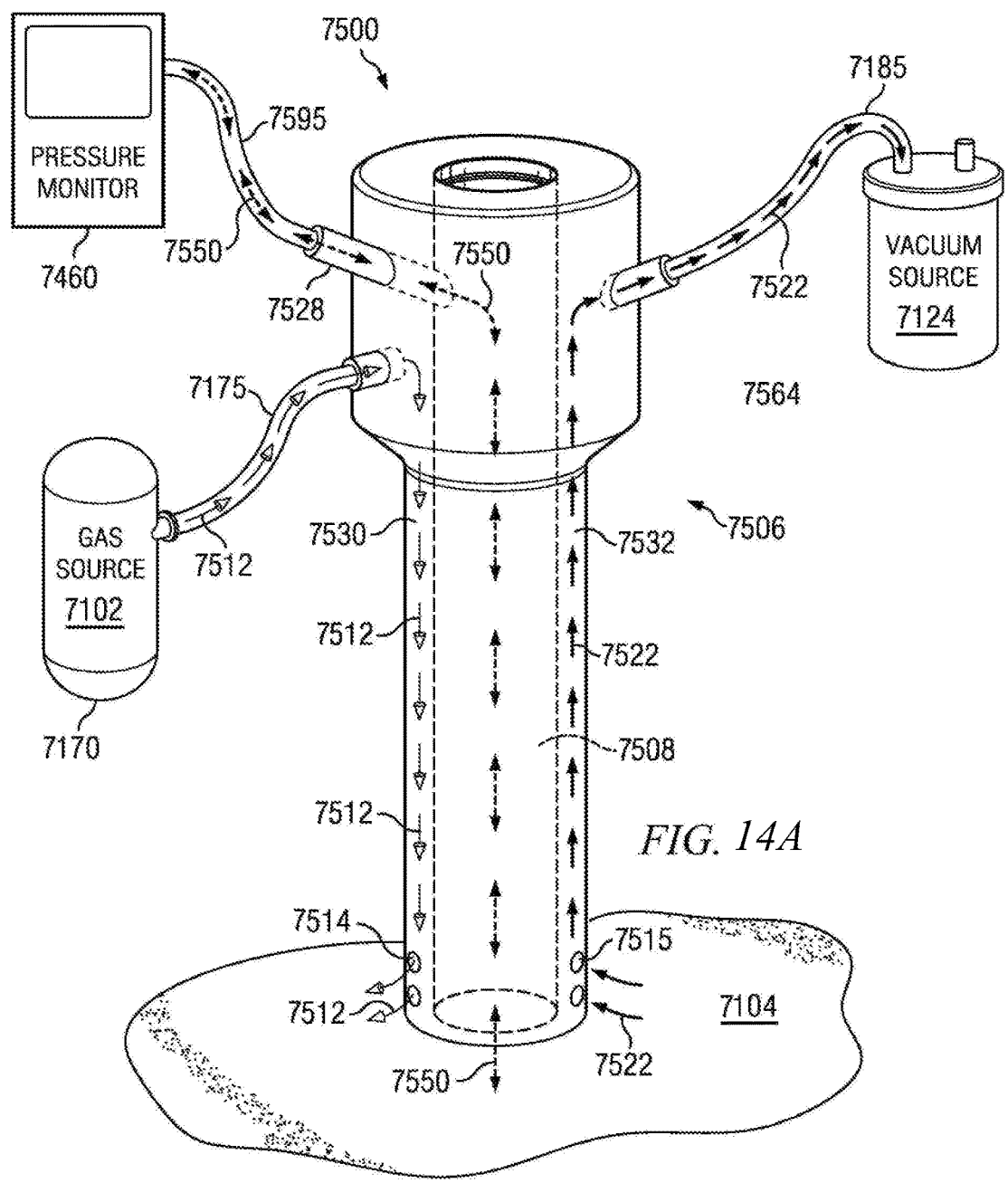

FIGS. 14A and 14B illustrate one embodiment of a system 7500 to supply an insufflation fluid 7102 to a patient cavity 7104 that uses a trocar having an inner lumen and an outer lumen with a plurality of chambers in which one of the chambers in the outer lumen allows for the insufflation fluid to be delivered to the patient cavity, the other chamber in the outer lumen provides a path for smoke to be removed from the patient cavity, and the inner lumen allows pressure measurement of the patient cavity.

System 7500 includes trocar 7506, which is analogous to trocar 7306, with analogous portions having analogous reference numerals. System 7500 is analogous to system 7300 except for the addition of pressure measurement system 7460 coupled by a conduit 7595 and connection 7598 to inner lumen 7508 of trocar 7506. Connection 7598 may be any suitable connection for coupling inner lumen 7508 to conduit 7595.

In operation, system 7500 performs similarly to system 7300. In particular, insufflation fluid 7102 is delivered to patient cavity 7104 from insufflation fluid source 7170 through conduit 7175 and chamber 7530 of outer lumen 7510, as indicated by arrows 7512. Insufflation fluid 7102 enters patient cavity 7104 via apertures 7514 in an outer wall 7518 of the trocar 7506.

The other chamber in outer lumen 7510, chamber 7532, allows for smoke in patient cavity 7104 to be removed using the same trocar 7506 as is used for supplying insufflation fluid 7102 to patient cavity 7104. Smoke is removed from patient cavity 7104 through apertures 7515 through chamber 7532 of outer lumen 7510 via connection 7520, which couples chamber 7532 of outer lumen 7508 to conduit 7585, as indicated by arrows 7522. The smoke from patient cavity 7104 enters chamber 7532 of outer lumen 7108 through aperture 7515 in outer wall 7518 of trocar 7506. The smoke can be vented into the operating room, filtered into the operating room, or vented out of the operating room via a vacuum source 7124.

In addition, inner lumen chamber 7508 allows for pressure measurement by creating a direct connection from patient cavity 7104 to a monitor 7460 external to the patient, as indicated by bi-directional arrows 7550. The direct connection has a minimal pressure drop to ensure accurate measurement.

Figure 15B:
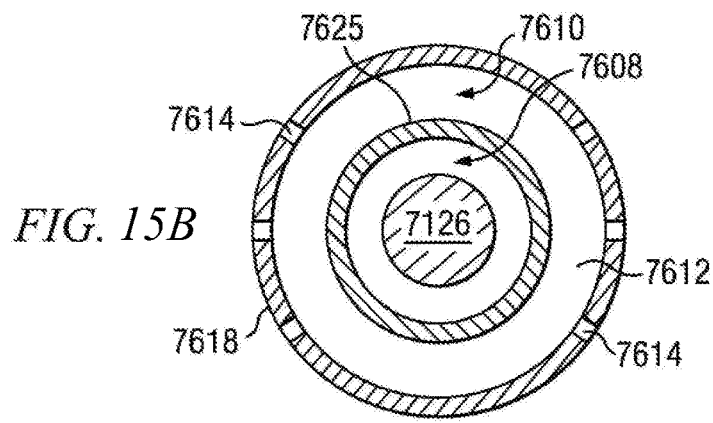
FIGS. 15A and 15B illustrate one embodiment of a system to supply an insufflation fluid to a patient cavity that uses a trocar having an inner lumen and an outer lumen in which the outer lumen allows for the insufflation fluid to be delivered to the patient cavity and the inner lumen allows pressure measurement of the patient cavity.
Figure 15A:
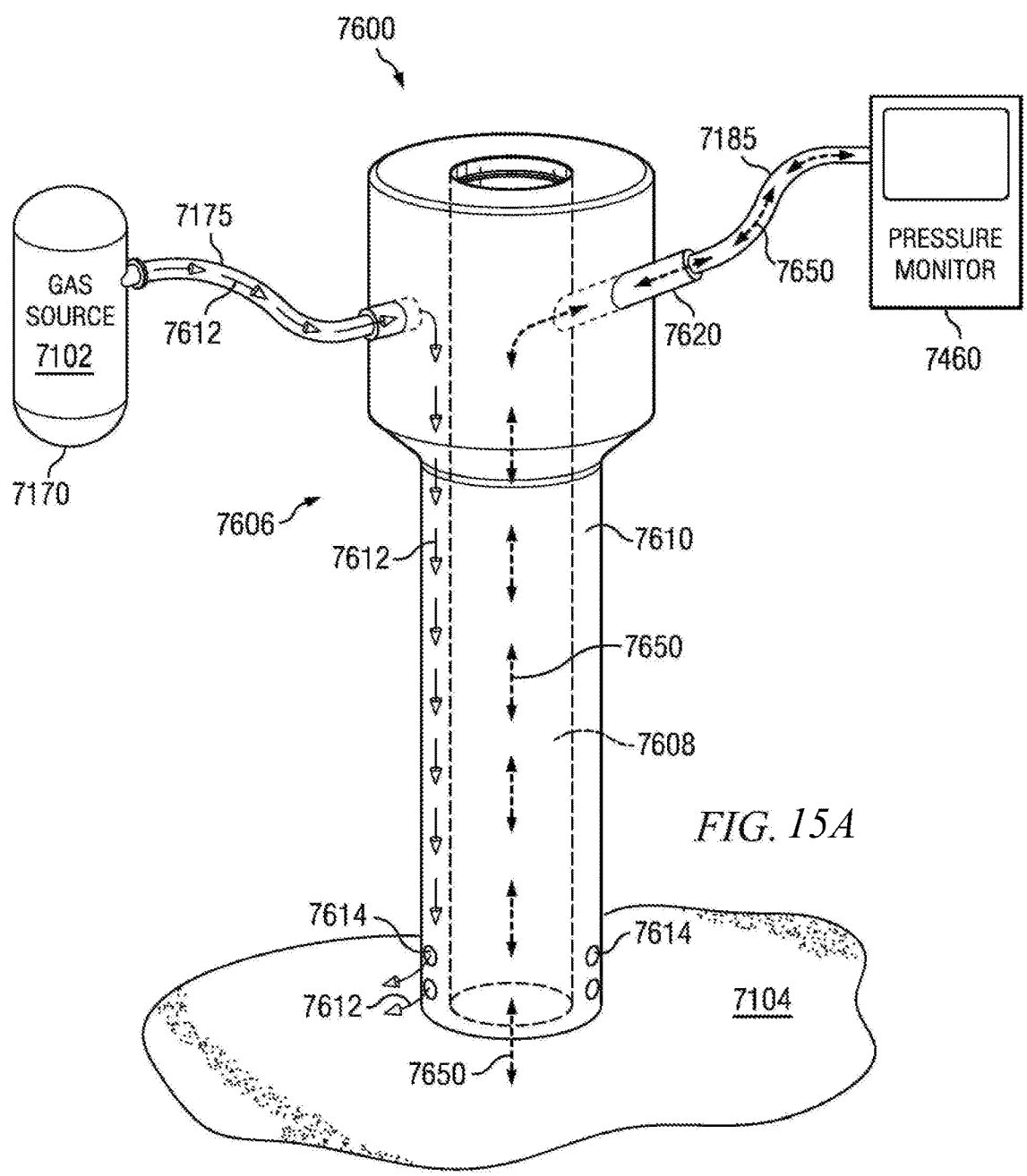

FIGS. 15A and 15B illustrate one embodiment of a system 7600 to supply an insufflation fluid 7102 to a patient cavity 7104 that uses a trocar having an inner lumen and an outer lumen in which the outer lumen allows for the insufflation fluid to be delivered to the patient cavity and the inner lumen allows pressure measurement of the patient cavity.

System 7500 includes trocar 7506, which is analogous to trocar 7106, with analogous portions having analogous reference numerals. System 7600 is analogous to system 7100, with analogous portions having analogous reference numerals, except that system 7600 includes monitor 7460 for measuring pressure. System 7600 also includes a suitable connection 7620 for such pressure measurement that couples inner lumen 7608 of trocar 7606 to conduit 7185.

In operation, insufflation fluid 7102 is delivered to patient cavity 7104 from insufflation fluid source 7170 through conduit 7175 and outer lumen 7610, as indicated by arrows 7612. Insufflation fluid 7102 enters patient cavity 7104 via apertures 7614 in outer wall 7618 of the trocar 7606.

Inner lumen 7608 allows for pressure measurement by creating a direct connection from patient cavity 7104 to a monitor 7460 external to the patient, as indicated by bi-directional arrows 7650. The direct connection has a minimal pressure drop to ensure accurate measurement.

Figure 16B:
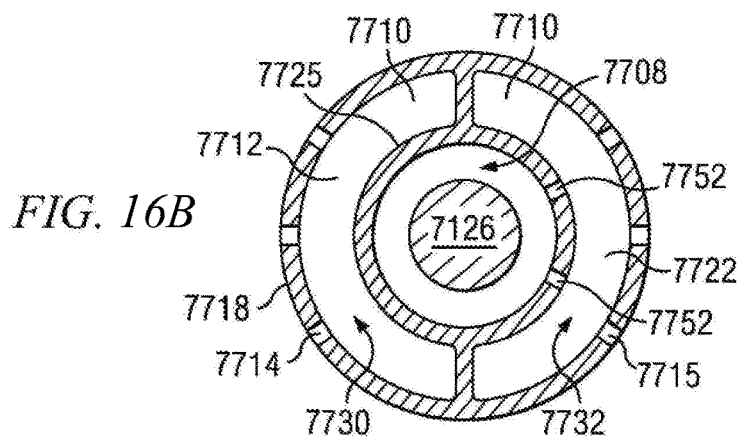
FIGS. 16A and 16B illustrate one embodiment of a system to supply an insufflation fluid to a patient cavity that uses a trocar having an inner lumen and an outer lumen with a plurality of chambers in which one of the chambers in the outer lumen allows for the insufflation fluid to be delivered to the patient cavity, the other chamber in the outer lumen allows pressure measurement of the patient cavity, and the inner lumen provides a path for smoke to be removed from the patient cavity.
Figure 16A:
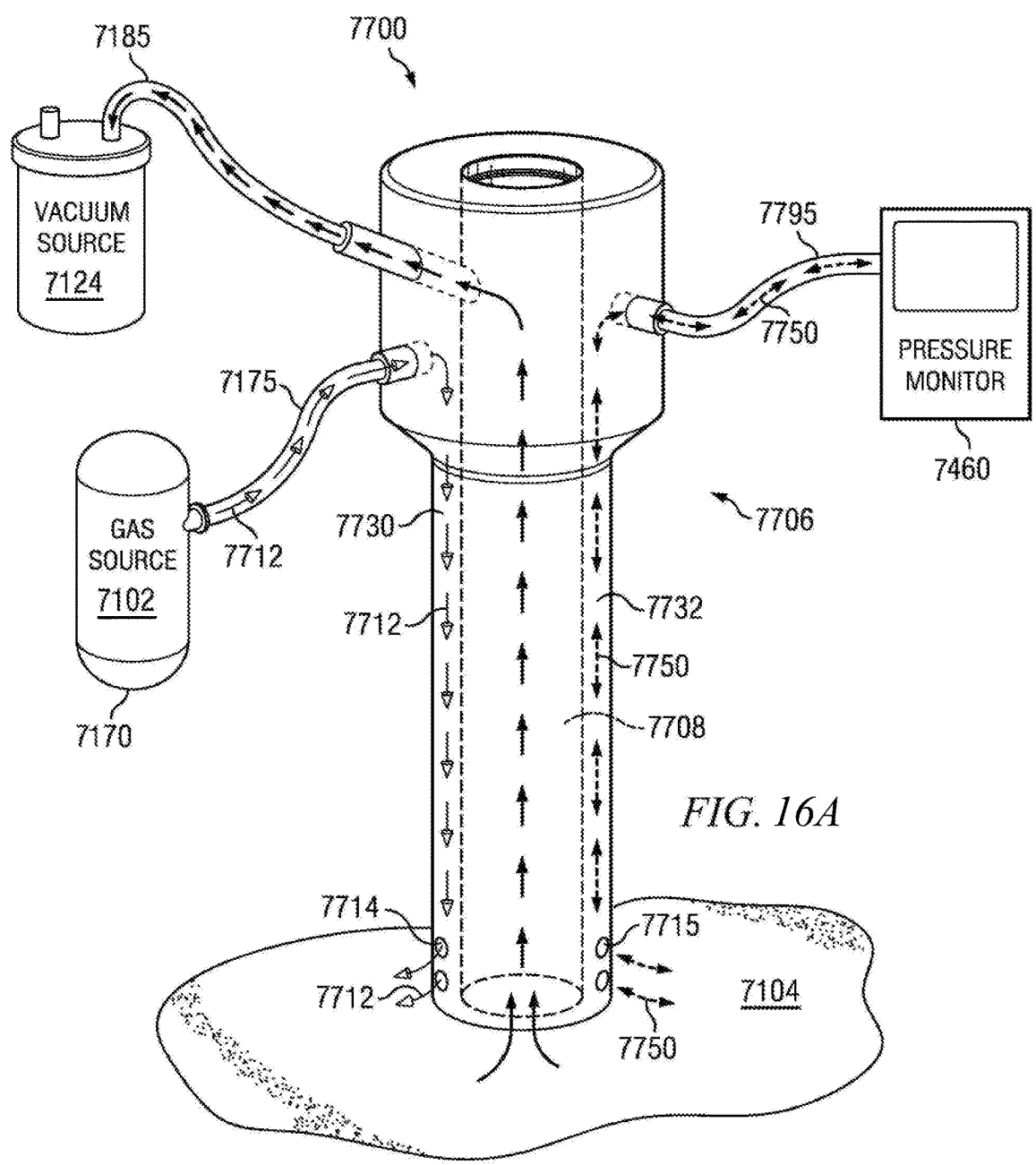

FIGS. 16A and 16B illustrate one embodiment of a system to supply an insufflation fluid to a patient cavity that uses a trocar having an inner lumen and an outer lumen with a plurality of chambers in which one of the chambers in the outer lumen allows for the insufflation fluid to be delivered to the patient cavity, the other chamber in the outer lumen allows pressure measurement of the patient cavity, and the inner lumen provides a path for smoke to be removed from the patient cavity.

System 7700 includes trocar 7706, which is analogous to trocar 7506, with analogous portions having analogous reference numerals. System 7700 is analogous to the system 7500 except that pressure measurement occurs through outer chamber 7732 of trocar 7700 as opposed to through inner lumen 7508 of system 7500, and smoke is removed from patient cavity 7104 through inner lumen 7708 of trocar 7700 as opposed to through outer chamber 7552 of system 7500. A connector 7721 couples conduit 7185 to inner lumen 7730.

In operation, insufflation fluid 7102 is delivered to patient cavity 7104 from insufflation fluid source 7170 through conduit 7175 and chamber 7730 of outer lumen 7710, as indicated by arrows 7712. Insufflation fluid 7102 enters patient cavity 7104 via apertures 7714 in an outer wall 7718 of the trocar 7706.

The other outer lumen chamber, chamber 7732, allows for pressure measurement by creating a direct connection from patient cavity 7104 to a monitor 7460 external to the patient, as illustrated by bi-directional arrows 7750. The direct connection has a minimal pressure drop to ensure accurate measurement. Outer lumen 7710 may or may not be connected to inner lumen 7708 via one or more holes 7752 in inner wall 7725.

Inner lumen 7708 allows for smoke to be removed via an open gas tubing connection 7721 to inner lumen 7708. The smoke can be vented into the operating room, filtered into the operating room, or vented out of the operating room via vacuum source 7124. Inner lumen 7708 also allows for the insertion of a surgical instrument 7126 at the same time as smoke is being removed.

Thus, the systems of FIG. 10A through 16B allow removal of smoke and/or pressure measurements while also providing a path from an insufflation fluid to a patient cavity using a single trocar. In some embodiments this avoids the use of multiple trocars in a patient at the same time; however, the teachings of the present disclosure recognize that the described systems and methods may be used in conjunction with the use of multiple trocars if desired.

Additional details of the systems described in FIGS. 10A-16B are described below for insufflation fluid 7102, insufflation fluid source 7170, trocars 7106-7706, open gas tubing connection 7120, vacuum break 7166, connection 7164, conduit 7175, conduit 7185, vacuum source 7124, and surgical instrument 126.

Insufflation fluid 7102 may be any suitable gas used for insufflation purposes. In one example, insufflation case is carbon dioxide. Insufflation fluid source 7170 may be any suitable source of insufflation fluid 7102 at any suitable pressure.

Trocar described and depicted in FIGS. 10-16 (trocars 7106, 7206, 7306, 7406, 7506, 7606, and 7707) can be any suitable trocar that includes an inner and outer lumen as described herein. All trocars described herein may be open or closed at the distal end, as the application of the trocar would allow. Further the trocars may or may not include apertures in their inner wall separating the outer lumen from the inner lumen. Further all trocars described herein may be formed according to features described in the '219 patent, the '112 patent, and/or the '189 patent. Further, trocars 106-706 may be formed with a heater and/or humidifier therein.

Vacuum break 7166 may be a flapper valve that remains closed when the patient cavity is under a pressure higher than the surrounding atmosphere. The closed valve will not allow insufflation fluid to leak into the atmosphere. When the pressure in patient cavity 7104 drops to atmospheric pressure or lower the flapper valve 7166 will open relieving most of the negative pressure within the body cavity.

Conduit 7175 may be any suitable conduit for providing an insufflation fluid to a portion of a trocar. An example of conduit 7175 includes flexible PVC tubing.

Conduit 7185 may be any suitable conduit for providing a vacuum to a portion of a trocar. An example of conduit 7185 is flexible PVC tubing.

Vacuum source 7124 is any suitable device that can apply a relative negative pressure to a portion of a trocar for removal of smoke from a patient cavity. Examples of vacuum source 7124 include a stand-alone vacuum pump or a centralized hospital vacuum system.

Surgical instrument 7126 may be any suitable instrument that may be used in surgery, including an obturator used to make an incision to obtain access to a body cavity.

This disclosure further contemplates measuring the pressure of a body cavity when delivering insufflation fluid through one or more medical appliances. As one example, insufflation fluid may be delivered to the patient cavity through a trocar that is inserted through a medical port such as a GelPort. As described above in reference to FIG. 9, a GelPort may include a seal (also referred to herein as a "cap") and a retractor. As is also described above in reference to FIG. 9, the seal may comprise a penetrable material that permits the insertion of one or more other medical appliances/instruments (e.g., trocar 6022, a grasper, etc.) therethrough. Such an example is described and illustrated in reference to FIG. 17.

Figure 17:
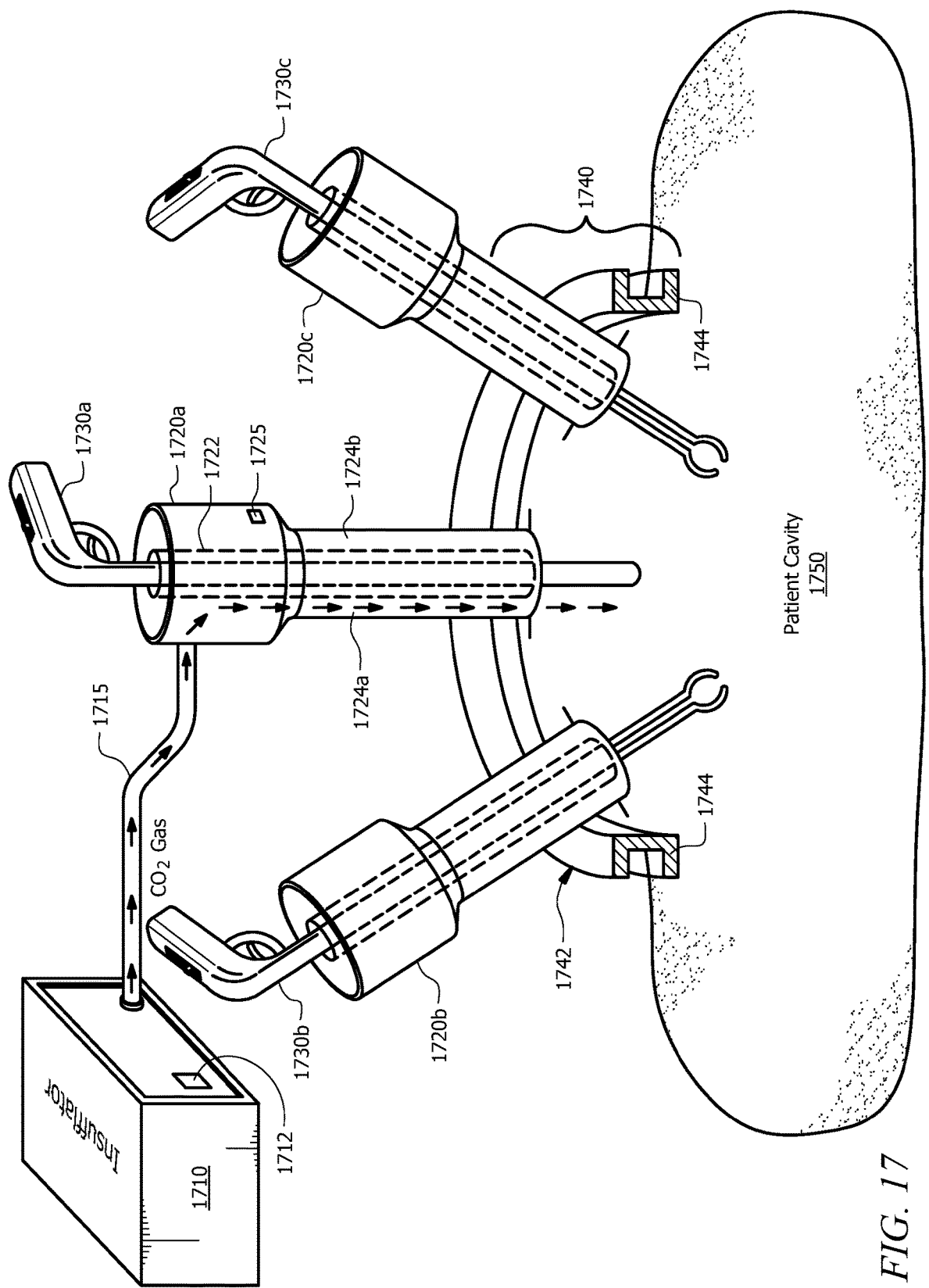
FIG. 17 is a schematic diagram of a system for delivering insufflation fluid to a patient cavity via a trocar and an access port.

FIG. 17 illustrates a system 1700 for delivering insufflation fluid to a patient cavity 1750 via a trocar 1720a inserted through a multiple access port, such as a GelPort described above in reference to FIG. 9. As will be understood by one of ordinary skill in the art, real-time pressure sensing is of critical importance in certain medical procedures (e.g., TAMIS) procedures wherein the volume of insufflation is restricted given the size of the patient cavity. Inadvertent loss of insufflation during such procedures greatly affects the ability of a medical professional to explore and/or view the site to be treated or observed.

One or more trocars 1720 (or other medical appliances) may be inserted through GelPort 1740 to provide an operator (e.g., a surgeon) with access to patient cavity 1750. As shown in FIG. 17, three trocars 1720 (i.e., trocars 1720a, 1720b, and 1720c) penetrate a seal 1742 of GelPort 1740 such that insufflation fluid and/or medical appliances/instruments (e.g., grasper, scope) reach a desired portion of patient cavity 1750. In addition to seal 1742, GelPort 1744 also includes, in some embodiments, a retractor 1744 configured to hold or maintain an incision site open to a desired level of openness.

Similar to other insufflation delivery systems described and depicted herein, system 1700 includes at least one insufflator 1710, a trocar 1720a, and a conduit 1715 coupling insufflator 1710 to trocar 1720a that facilitates delivery of insufflation fluid from insufflator 1710 to trocar 1720a. System 1700 also includes one or more pressure sensors. As shown in FIG. 17, system 1700 includes pressure sensors 1712 and 1725. Sensor 1712 may be disposed in, on, or through insufflator 1710 and be configured take pressure measurements indicative of a pressure of patient cavity 1750. Sensor 1725 may be disposed in, on, or through trocar 1720a and be configured take pressure measurements indicative of a pressure of patient cavity 1750. Pressure sensor 1725 may be disposed in any suitable position in, on, or through trocar 1720a, including but not limited to the positions described and depicted in FIGS. 2A-4B and FIG. 6. This disclosure also recognizes positioning pressure sensor 1725 in, on, or through any suitable chamber defined by walls of a trocar. For example, this disclosure contemplates positioning pressure sensor 1725 in, on, or through any of the following: an inner lumen of a trocar (e.g., inner lumen 108 of FIGS. 10A and 10B), an outer lumen of a trocar (e.g., outer lumen 110 of FIGS. 10A and 10B), or any partitioned portion of an outer lumen of a trocar (e.g., chambers 330 & 332 of FIG. 12B).

In operation, an operator (e.g., a surgeon) penetrates seal 1742 of GelPort 1740 with a trocar (e.g., trocar 1720a) and couples the penetrating trocar 1720a to an insufflator 1710 using a conduit 1715 to ensure a fluid connection therebetween. The operator may then initiate insufflation of patient cavity 1750 using insufflator 1710, wherein insufflation fluid is discharged from insufflator 1710 to conduit 1715, which in turn directs the insufflation fluid through trocar 1720a, which in turn delivers the insufflation fluid to patient cavity 1750. As shown in FIG. 17, trocar 1720a includes an inner lumen 1722 and an outer lumen 1724 and insufflation fluid is delivered to patient cavity 1750 via outer lumen 1724. In particular embodiments, such as that illustrated in FIG. 17, insufflation fluid is delivered to patient cavity 1750 via a particular chamber (e.g., chamber 1724a) of outer lumen 1724 (as indicated by the arrows in FIG. 17).

In alternative embodiments, insufflation fluid may be directed from conduit 1715 to inner lumen 1722 of trocar 1720a before being delivered to patient cavity 1750. Given that inner lumen 1722 may also accommodate one or more medical instruments (e.g., a grasper), trocar 1720a may also include a suitable seal through which an instrument is inserted to limit or restrict the escape of insufflation fluid from the proximal end of trocar 1720a.

As described above, operators (and or assistants thereof) monitor the pressure of a patient cavity to ensure the patient cavity 1750 is properly insufflated when performing a surgical procedure. These pressure measurements may be taken by pressure sensors 1710 and/or 1725. In some embodiments, one pressure sensor (e.g., sensor 1725) may serve as a primary sensor and another pressure sensor (e.g., sensor 1710) may serve as a backup sensor such that insufflator 1710 supplies insufflation fluid to patient cavity 1750 based on pressure measurements taken by sensor 1725 unless and until sensor 1725 is determined to be inaccurate or otherwise unreliable. Upon making such determination, insufflator 1710 may supply insufflation fluid to patient cavity 1750 based on pressure measurements taken by sensor 1710. In some other embodiments, sensor 1710 may be the primary pressure sensor and sensor 1725 may be the backup pressure sensor.

Figure 18:
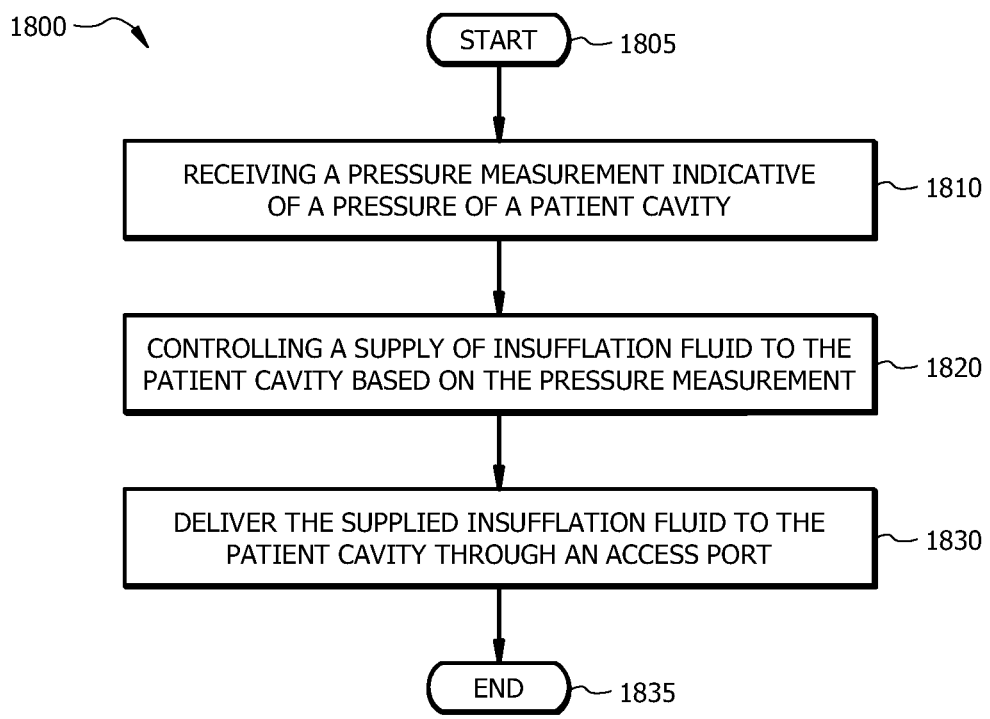
FIG. 18 is a flow chart illustrating a method for delivering insufflation fluid to a patient cavity using the system of FIG. 17.

FIG. 18 illustrates a method 1800 of delivering insufflation fluid to a patient cavity using system 1700 of FIG. 17. In some embodiments, the method 1800 begins at a step 1805 and continues to a step 1810. At step 1810, system 1700 receives a pressure measurement indicative of a pressure of patient cavity 1850. In some embodiments, the pressure measurement is taken by a pressure sensor (e.g., pressure sensor 1810, 1825). The sensor taking such measurement may be a primary and/or backup pressure sensor. As described above, the component of system 1700 that receives the pressure measurement may, in certain embodiments, be insufflator 1710. As described in reference to FIG. 7A, insufflator 1710 may include components (e.g., memory, processor, interfaces) necessary to receive, and act on, pressure measurement information. Upon completion of step 1810, the method 1800 may proceed to a step 1820.

At step 1820, system 1700 controls a supply of insufflation fluid to patient cavity 1750 based on the pressure measurement received at step 1710. In some embodiments, the component of system 1700 that executes step 1820 is insufflator 1710. In such embodiments, a processor of insufflator 1710 may execute step 1820. Upon completion of step 1820, the method 1800 may proceed to a step 1830.

At step 1830, system 1700 delivers the supplied insufflation fluid to patient cavity 1750 via access port 1740. In some embodiments, the component that delivers the insufflation fluid to patient cavity 1750 is trocar 1720*a*. As described above, trocar 1720*a* may be configured to penetrate a seal 1742 of access port 1740, thereby providing a flow path for the insufflation fluid from trocar 1720*a* to patient cavity 1750. In some embodiments, the insufflation fluid is directed through an inner lumen (e.g., lumen 1722) of trocar 1720*a* and is discharged into patient cavity 1750. In other embodiments, the insufflation fluid is directed through an outer lumen (e.g., lumen 1724) (or a chamber thereof) of trocar 1720*a* and is discharged into patient cavity 1750. Upon completion of step 1830, the method 1800 may proceed to an end step 1835.

In some embodiments, method 1800 may include only a subset of the steps described above. In other embodiments, method 1800 may include steps in addition to those described above. As an example, method 1800 may include one or more of the following steps: (1) directing, by conduit 1715, the insufflation fluid from insufflator 1710 to trocar 1720*a*; (2) determining, by a sensor other than the one that took the pressure measurement at step 1810, a pressure measurement indicative of a pressure of the patient cavity; (3) determining, by insufflator 1710, that the pressure measurement taken at step 1810 is inaccurate or otherwise unreliable; and (4) controlling the supply of the insufflation fluid by insufflator 1710 to patient cavity 1850 based on the pressure measurement determined by the other sensor identified in preceding additional step (2).

Although FIGS. 1-18 have been described above as including particular steps and/or components, the method and systems of these FIGURES may include any combination of any of the described steps and/or components and any of the options or features described herein, as would be understood by one of ordinary skill in the art. For example, any of the steps, options, or features described in reference to one figure may be utilized in combination with any number of other steps, options, or features described in reference to another figure, as would be understood by one of ordinary skill in the art.

Although the embodiments in the disclosure have been described in detail, numerous changes, substitutions, variations, alterations, and modifications may be ascertained by those skilled in the art. It is intended that the present disclosure encompass all such changes, substitutions, variations, alterations, and modifications. Additionally, one or more features described herein may be combined with one or more embodiments also described herein. For example, a primary and/or a backup sensor as described above and illustrated in reference to FIGS. 2A-8 may be combined with the trocars shown and described with reference to FIGS. 10A-16B. As another example, the trocars illustrated and described with reference to FIGS. 10A-16B may also be combined with the system described and illustrated in FIG. 17 (e.g., replace trocar 1720*a* of FIG. 17 with trocar 7600 of FIG. 15*a*). As yet another example, the system described and illustrated in FIG. 17 may incorporate features from FIGS. 2A-8 (e.g., sensor 1725 of FIG. 17 may be repositioned/relocated in, on, or through trocar as illustrated and described in FIGS. 2*a*-6).

What is claimed is:

1. A system comprising:
   an insufflator configured to supply insufflation fluid to a patient cavity, the insufflator comprising a processor and a computer-readable media having logic stored thereon;
   an access port comprising a cap and a retractor, the access port facilitating access therethrough to the patient cavity, wherein the cap is formed of a penetrable material that seals a mouth of the retractor;
   a primary pressure sensor located in, on, or through the access port and configured to determine a pressure measurement indicative of a pressure of the patient cavity;
   a trocar configured to:
   receive the insufflation fluid supplied by the insufflator; and
   deliver the insufflation fluid to the patient cavity via the access port;
   wherein:
   the insufflator is communicatively coupled to the primary pressure sensor; and
   the logic stored on the computer-readable media is configured, when executed on the processor, to:
   receive the pressure measurement from the primary pressure sensor; and
   control the supply of the insufflation fluid to the patient based on the pressure measurement from the primary pressure sensor.

2. The system of claim 1, wherein at least a portion of the trocar is configured to penetrate the cap of the access port thereby directing the insufflation fluid to the patient cavity.

3. The system of claim 1, wherein the trocar receives the insufflation fluid from a conduit comprising a first end and a second end, wherein the first end is coupled to the insufflator and the second end is coupled to the trocar.

4. The system of claim 1, wherein the trocar comprises an outer tubular member disposed about an inner tubular member, wherein the inner tubular member is separated from the outer tubular member by an inner wall.

5. The system of claim 4, wherein the outer tubular member is partitioned into at least a first chamber and a second chamber, wherein:
- the first chamber is separated from the second chamber; and
- the first chamber and the second chamber are defined by the inner wall and an outer wall of the outer tubular member.

6. The system of claim 4, wherein the insufflation fluid is delivered to the patient cavity via the outer tubular member.

7. The system of claim 4, wherein the insufflation fluid is delivered to the patient cavity via the inner tubular member.

8. The system of claim 1, wherein the trocar comprises the primary pressure sensor.

9. The system of claim 8, wherein the logic stored on the computer-readable media is further configured, when executed on the processor, to:
- determine that the pressure measurement from the primary pressure sensor is inaccurate and, in response, control the supply of the insufflation fluid by the insufflator to the patient cavity based on the pressure measurement determined by the backup pressure sensor rather than the pressure measurement determined by the primary pressure sensor.

10. The system of claim 1, wherein the insufflator comprises the primary pressure sensor.

11. The system of claim 1, wherein the system further comprises a backup pressure sensor communicatively coupled to the insufflator, the backup pressure sensor being configured to determine a pressure measurement indicative of a pressure of the patient cavity.

12. A method of supplying insufflation fluid to a patient cavity, the method comprising:
- receiving, from a primary pressure sensor, a pressure measurement indicative of a pressure of a patient cavity;
- controlling, by an insufflator, a supply of the insufflation fluid to the patient cavity based on the pressure measurement from the primary pressure sensor; and
- delivering, by a trocar, the supplied insufflation fluid to the patient cavity via an access port, wherein:
  - the primary pressure sensor is located in, on, or through the access port;
  - the access port comprises a seal and a retractor, the seal configured to be removably coupled to at least one end of the retractor; and
  - the access port facilitates access therethrough to the patient cavity.

13. The method of claim 12, wherein delivering the insufflation fluid via the access port comprises penetrating, by at least a portion of the trocar, the seal of the access port to permit access therethrough to the patient cavity.

14. The method of claim 12, further comprising:
- directing, by a conduit, the insufflation fluid from the insufflator to the trocar.

15. The method of claim 12, wherein delivering the insufflation fluid to the patient cavity comprises directing the insufflation fluid through an outer tubular member of the trocar, wherein the outer tubular member is disposed about an inner tubular member, the inner tubular member being separated from the outer tubular member by an inner wall.

16. The method of claim 15, wherein delivering the insufflation fluid to the patient cavity comprises directing the insufflation fluid through a first or a second chamber of the outer tubular member, wherein the first chamber is separated from the second chamber and the first chamber and the second chamber are defined by the inner wall and an outer wall of the outer tubular member.

17. The method of claim 12, wherein delivering the insufflation fluid to the patient cavity comprises directing the insufflation fluid through an inner tubular member of the trocar, wherein:
- the trocar further comprises an outer tubular member disposed about the inner tubular member, the inner tubular member being separated from the outer tubular member by an inner wall.

18. The method of claim 12, wherein the primary pressure sensor is comprised within one of the insufflator or the trocar.

19. The method of claim 12, further comprising determining, by a backup pressure sensor, a pressure measurement indicative of a pressure of the patient cavity.

20. The method of claim 19, further comprising:
- in response to determining that the pressure measurement from the primary pressure sensor is inaccurate controlling the supply of the insufflation fluid by the insufflator to the patient cavity based on the pressure measurement determined by the backup pressure sensor rather than the pressure measurement determined by the primary pressure sensor.

* * * * *